(12) United States Patent
Takahashi

(10) Patent No.: US 9,402,551 B2
(45) Date of Patent: Aug. 2, 2016

(54) PULSE DETECTOR WITH UNWORN-STATE DETECTION

(75) Inventor: Yusuke Takahashi, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 714 days.

(21) Appl. No.: 13/369,582

(22) Filed: Feb. 9, 2012

(65) Prior Publication Data

US 2012/0215115 A1   Aug. 23, 2012

(30) Foreign Application Priority Data

Feb. 23, 2011   (JP) ................. 2011-036801

(51) Int. Cl.
*A61B 5/02* (2006.01)
*A61B 5/024* (2006.01)
*A61B 5/11* (2006.01)
*A61B 5/00* (2006.01)

(52) U.S. Cl.
CPC ......... *A61B 5/02416* (2013.01); *A61B 5/02438* (2013.01); *A61B 5/1118* (2013.01); *A61B 5/721* (2013.01)

(58) Field of Classification Search
CPC ............... A61B 5/681; A61B 5/02416; A61B 5/02438; A61B 5/1118; A61B 5/721; A63B 2071/0663; A63B 2220/40
USPC ......................................... 600/483, 500–503
See application file for complete search history.

(56) References Cited

U.S. PATENT DOCUMENTS

| | | | |
|---|---|---|---|
| 5,515,858 A * | 5/1996 | Myllymaki | 600/301 |
| 5,810,736 A * | 9/1998 | Pail | 600/500 |
| 6,155,983 A * | 12/2000 | Kosuda et al. | 600/500 |
| 6,198,951 B1 | 3/2001 | Kosuda et al. | |
| 7,438,688 B2 | 10/2008 | Kobayashi et al. | |
| 2003/0045784 A1 * | 3/2003 | Palatnik et al. | 600/323 |
| 2003/0045802 A1 | 3/2003 | Kato | |
| 2004/0087845 A1 * | 5/2004 | Katarow et al. | 600/323 |
| 2004/0186387 A1 | 9/2004 | Kosuda et al. | |
| 2005/0075553 A1 | 4/2005 | Sakai et al. | |
| 2007/0016381 A1 * | 1/2007 | Kamath et al. | 702/19 |
| 2009/0018454 A1 * | 1/2009 | Hung | 600/500 |
| 2009/0270744 A1 * | 10/2009 | Prstojevich et al. | 600/503 |

FOREIGN PATENT DOCUMENTS

| | | |
|---|---|---|
| JP | 2003-070757 A | 3/2003 |
| JP | 2005-131426 A | 5/2005 |
| JP | 2005-160640 A | 6/2005 |
| JP | 2005-198829 A | 7/2005 |
| JP | 2005-211301 A | 8/2005 |
| JP | 3689914 B2 | 8/2005 |
| JP | 2007-054471 A | 3/2007 |
| JP | 2009-183519 A | 8/2009 |
| JP | 2010-098356 A | 4/2010 |

* cited by examiner

*Primary Examiner* — Jacqueline Cheng
*Assistant Examiner* — Puya Agahi
(74) *Attorney, Agent, or Firm* — Global IP Counselors, LLP

(57) ABSTRACT

To detect whether the pulse detector is in an unworn state, the pulse detector is provided for detecting a pulse signal that originates in the pulse of a subject has a pulse wave sensor, a pulse wave sensor sensitivity adjustment section that adjusts the sensitivity of the pulse wave sensor, a body movement sensor, and an unworn-state detector that detects that the pulse detector has been removed from the subject and is in an unworn state, on the basis of the sensitivity of the pulse wave sensor sensitivity adjustment section and a body movement sensor signal outputted from the body movement sensor.

9 Claims, 10 Drawing Sheets

PULSE DETECTOR WITH UNWORN-STATE DETECTION

CROSS-REFERENCE TO RELATED APPLICATIONS

This application claims priority to Japanese Patent Application No. 2011-036801 filed on Feb. 23, 2011. The entire disclosure of Japanese Patent Application No. 2011-036801 is hereby incorporated herein by reference.

BACKGROUND

1. Technological Field

The present invention relates to a pulse detector and the like.

2. Background Technology

A pulse detector is a device for detecting a pulse originating from a human heartbeat, and is a device for removing as noise a signal component generated by the effects of human body movements from a signal (pulse wave signal) received from a pulse wave sensor worn on, e.g., the arm, palm, finger, or the like to detect a signal (pulse signal) derived from a heartbeat.

A pulse rate meter of a type that is worn on a human finger or wrist is disclosed in, e.g., Patent Documents 1 to 3.

There is also a pulse rate meter equipped with an acceleration sensor, and the pulse rate meter is used as a biological information measuring device provided with an activity meter, a pedometer, or another activity measurement function, an example of which is described in Patent Document 4. The use of such a biological information measuring device allows a measured person to manage his or her own pace distribution during activity, check the number of burned calories after activity, and perform other tasks to ascertain the amount of activity performed.

Patent Document 5 discloses a technique for judging the existence of subject motion on the basis of the output signal of an acceleration sensor or a gyro sensor.

Japanese Laid-open Patent Publication No. 2005-198829 (Patent Document 1), Japanese Laid-open Patent Publication No. 2007-54471 (Patent Document 2), Japanese Laid-open Patent Publication No. 2005-131426 (Patent Document 3), Japanese Laid-open Patent Publication No. 2005-211301 (Patent Document 4), and Japanese Laid-open Patent Publication No. 2010-98356 (Patent Document 5) are examples of the related art.

SUMMARY

Problems to Be Solved by the Invention

When a pulse detector is performing a pulse detection operation for a subject (human or animal), the subject can remove and leave the pulse detector unworn. In such a case, the pulse detector refers to, e.g., information or the like that indicates a trend in the frequency of the pulse signal detected in the past, and continues processing in order to identify a pulse component. As a result, mistakes can occur when, e.g., an external noise component that shows behavior similar to the pulse component is errantly detected as a pulse component, when an incorrect pulsation count information is displayed, or when calories burned by activity by the subject are calculated and displayed on the basis of the pulsation count.

Even when the pulse detector has been left unworn, power consumption increases when the processes for displaying (notifying the subject) the pulsation count (biological information of the subject), the burned calories (accompanying information related to activity by the subject), and the like are continued.

In accordance with art described in Patent Documents 4 and 5, the pulse detector is, after a fashion, capable of detecting the existence of action by the subject. However, when, the subject is resting, for example, and more particularly, when the subject is completely still such as when the subject is sleeping, it is difficult to judge whether the subject has removed the pulse detector, or whether the subject is merely motionless.

It is possible to consider as a method for detecting an unworn state a method in which the pressing force on the pulse detector main unit is detected by a pressure sensor or the like, or a method in which the grounded (earthed) state of the pulse detector is detected. However, in the case that these methods are used, a special configuration (special structure) is required for detecting the worn state. Also, it is possible that the unworn state cannot be accurately detected because the cases in which, e.g., the ground (earth) section of the pulse detector is brought into contact with metal and brought into contact with the body are similar in terms of the ground potential detected by the ground section.

In accordance with at least one aspect of the invention, for example, the pulse detector is capable of detecting an unworn state. For example, the unworn state of the pulse detector can be detected with high accuracy without the use of a special configuration.

Means Used to Solve the Above-Mentioned Problems (1) A first aspect of the pulse detector of the invention is a pulse detector that detects a pulse signal originating from a pulse of a subject, the pulse detector characterized in including: a pulse wave sensor that outputs a pulse wave signal possibly including the pulse signal; a pulse wave sensor sensitivity adjustment section that adjusts the sensitivity of the pulse wave sensor on the basis of an input signal to the pulse wave sensor or the intensity of the pulse wave signal; a body movement sensor that detects body movement of the subject and outputs a body movement sensor signal originating from the body movement; and an unworn-state detector that detects an unworn state in which the pulse detector has been removed from the subject, on the basis of the sensitivity of the pulse wave sensor adjusted by the pulse wave sensor sensitivity adjustment section and the body movement sensor signal outputted from the body movement sensor.

In the present aspect, the unworn detector detects the unworn state of the pulse detector on the basis of the sensitivity of the pulse wave sensor adjusted by the pulse wave sensor sensitivity adjustment section and the body movement sensor signal outputted from the body movement sensor.

In a state in which the pulse detector is worn by the subject and pulse detection processing is being carried out, the sensitivity set by the pulse wave sensor sensitivity adjustment section is a value within a range generated during ordinary measurement. In contrast, in the case that the pulse detector is removed and unworn by the subject, there is a high possibility that the sensitivity will be out of the range (permissible range) generated during ordinary measurement.

In other words, when, e.g., the pulse detector is left unworn on a desk, there is a high possibility that light from indoor illumination or outdoor light that has entered through a window or the like (these will be generically referred to as external light) will be incident on the pulse wave sensor. External light is directly incident on the pulse detector, but the light used for pulse detection is reflected light (or scattered light, or indirectly incident light) that has been reflected by blood vessels. Therefore, the level of external light, which is direct light, is often greater than the level of reflected light used for pulse detection. Also, in the case that the pulse detector has been stored in a desk drawer or a bag, the level of the external light is near zero because external light is mostly blocked. In other words, in this case, the level of external light is sufficiently low in comparison with the level of reflected light used for pulse detection.

In other words, when the pulse detector is in an unworn state, it is highly possible that the intensity of the light (the level of the light) incident on the pulse wave sensor will be an intensity (level) in a range that is not possible during ordinary detection processing. At this time, the sensitivity of the pulse wave sensor is out of the range (permissible range) generated during ordinary measurement. Therefore, the sensitivity of the pulse wave sensor set by the pulse wave sensor sensitivity adjustment section can be used as important information for detecting the unworn state of the pulse detector.

When the pulse detector is in an unworn state, the level of the body movement sensor signal (signal originating from the body movement of the subject) outputted from the body movement sensor can be a level within a range that can be considered to be zero because there is no body movement.

Therefore, in the present aspect, the unworn state of the pulse detector is judged on the basis of the sensitivity of the pulse wave sensor and the body movement sensor signal. For example, when the sensitivity is out of the range (permissible range) generated during ordinary measurement and the level of the body movement sensor signal is a value within a range that can be considered to be zero, the unworn-state detector judges that the pulse detector is in an unworn state.

In the present aspect, it is possible to judge the unworn state with good precision because reference is made to the sensitivity of the pulse wave sensor adjusted by the pulse wave sensor sensitivity adjustment section, and dual use is made of the magnitude information of the body movement sensor signal to judge the unworn state. It is also possible to detect the unworn state of the pulse detector without the use of a special configuration.

(2) In another aspect of the pulse detector of the invention, the pulse detector further includes a frequency analyzer for performing frequency analysis at predetermined time intervals on the basis of the pulse wave signal or a filtered signal obtained by subjecting the pulse wave signal to filtering for suppressing noise included in the pulse wave signal, wherein the unworn-state detector detects the unworn state on the basis of the sensitivity of the pulse wave sensor adjusted by the pulse wave sensor sensitivity adjustment section, the body movement sensor signal outputted from the body movement sensor, and the result of the frequency analysis of the pulse wave signal performed by the frequency analyzer.

In the present aspect, the unworn-state detector judges the unworn state of the pulse detector with further reference to the results of the frequency analysis of the pulse wave sensor performed by the frequency analyzer, in addition to the sensitivity of the pulse wave sensor and the body movement sensor signal. The precision of unworn state detection is thereby further improved.

When the pulse detector is worn by the subject and pulse detection processing is being carried out, it is possible that the pulse wave signal outputted from the pulse wave sensor will include a pulse signal that has periodicity and that originates from the pulse of a subject, and a body movement sensor signal that has periodicity which originates in periodic body movement of the subject.

When the frequency of the pulse wave signal is resolved to analyze the frequency spectrum, a periodic signal appears in a specific frequency position on the frequency axis. Therefore, the state of the pulse detector is highly likely to be in a non-unworn state in the case that, e.g., the frequency spectrum of the pulse signal with a large signal value is present.

A frequency spectrum in which a pulse signal with large signal value and a body movement sensor signal with a large signal value are both present appears when the subject is in a state of constant (periodic) activity (e.g., a state in which the subject is walking with a fixed pitch while regularly swinging the arms). Therefore, when a frequency spectrum having both a pulse signal with large signal value and a body movement sensor signal with a large signal value appears, there is a high possibility that the pulse detector is in a non-unworn state.

On the other hand, there is a high possibility that the pulse detector is in an unworn state in the case that there is no spectrum at or above a predetermined threshold in the frequency spectrum obtained as a result of frequency analysis of the pulse wave signal, i.e., in the case that there is no spectrum whatsoever having valid information (a significant spectrum) about the pulse or activity state of the subject.

In this manner, the precision for judging the unworn state and non-unworn state can be increased by judging the unworn state with additional reference to the results of frequency analysis of the pulse wave signal that is performed by the frequency analyzer.

(3) In another aspect of the pulse detector of the invention, the unworn-state detector judges the unworn state to be in effect in the case that the sensitivity of the pulse wave sensor adjusted by the pulse wave sensor sensitivity adjustment section is out of a range permitted when the pulse signal is detected; the level of the body movement sensor signal outputted from the body movement sensor is within a range judged to be devoid of body movement of the subject; and the frequency spectrum obtained as a result of frequency analysis of the pulse wave signal does not include a spectrum equal to or greater than a first threshold value.

In the present aspect, an example of the judgment of the unworn-state detector is made apparent. In the present aspect, the unworn-state detector judges that the pulse detector is in an unworn state in the case that the sensitivity of the pulse wave sensor is out of a range permitted when the pulse signal is detected; when the level of the body movement sensor signal outputted from the body movement sensor is within a range judged to be devoid of body movement of the subject; and when the frequency spectrum obtained as a result of frequency analysis of the pulse wave signal does not include a spectrum equal to or greater than a first threshold value.

In accordance with the present aspect, the unworn state of the pulse detector can be detected with high accuracy without the use of a special configuration.

(4) In another aspect of the pulse detector of the invention, the unworn-state detector judges the unworn state to be in effect in the case that the sensitivity of the pulse wave sensor adjusted by the pulse wave sensor sensitivity adjustment section is out of a range permitted when the pulse signal is detected; the level of the body movement sensor signal outputted from the body movement sensor is within a range judged to be devoid of body movement of the subject; the frequency spectrum obtained as a result of frequency analysis of the pulse wave signal does not include a spectrum equal to or greater than a first threshold value; and an amount of noise included in the pulse wave signal is judged to be equal to or greater than a predetermined amount on the basis of the frequency spectrum.

In the present aspect, the condition stated in aspect (3) described above as "the frequency spectrum obtained as a result of frequency analysis of the pulse wave signal does not include a spectrum equal to or greater than a predetermined threshold value" can be substituted by the condition stated as "an amount of noise in the pulse wave signal is classified as intermediate or noisy on the basis of the frequency spectrum obtained as a result of frequency analysis of the pulse wave signal where, e.g., the amount of noise is classified as low, intermediate, or noisy."

Examples of the case in which the amount of noise in the pulse wave signal is judged to be low include the case in which a subject is in a state of constant (periodic) activity (e.g., a state of walking while regularly swinging the arms), and the case in which the subject is in a resting state.

The case in which the amount of noise in the pulse wave signal is judged to be "intermediate (moderate)" corresponds to the subject being, e.g., constantly active (e.g., walking while regularly swinging the arms) but also moving the wrist in irregular fashion or otherwise being aperiodically active.

The state of the frequency spectrum in such a case is a state in which, e.g., a pulse signal and body movement sensor signal both exist with signal values that exceed predetermined threshold values, and external noise (noise without periodicity) is present across a wide range on the frequency axis.

The case in which the amount of noise in the pulse wave signal is judged to be noisy corresponds to a case in which a state in which the subject is, e.g., doing irregular exercises, or playing basketball or other ball game. In this case, external noise having a signal value that exceeds a predetermined threshold value for judging external noise often appears in, e.g., a wide range of positions on the frequency axis in the frequency spectrum of the pulse wave signal.

Among the three classifications described above, there is a very high possibility that the pulse detector is being worn rather than unworn by the subject at least when the state of the pulse wave signal is "low noise." However, it is also possible to envision "a case in which the pulse detector is in an unworn state and a considerable amount of noise is generated for some reason" as a case in which the state of the pulse wave signal is "intermediate" or "noisy."

Therefore, in the present embodiment, the unworn-state detector judges that the pulse detector is in an unworn state in the case that the sensitivity of the pulse wave sensor is out of a range permitted when the pulse signal is detected, the level of the body movement sensor signal outputted from the body movement sensor is within a ranged judged to be devoid of subject body movement, and the amount of noise in the pulse wave signal is classified as being intermediate or noisy. The index for judging the amount of noise in the pulse wave signal can be the ratio of the signal values of two spectrums selected from among the main spectrum, can be statistical information (standard deviation, deviation value, or the like), or can be another parameter.

In accordance with the present aspect, the unworn state of the pulse detector can be detected with higher accuracy without the use of a special configuration. Also, in accordance with the present aspect, the unworn-state detector can differentiate between when the subject is, e.g., in a resting state (non-constant activity factors are not present) and when the pulse detector is in an unworn state.

(5) In another aspect of the pulse detector of the invention, the unworn-state detector performs a detection of the unworn state at predetermined time intervals, judges that the pulse detector is not in a unworn state in the case that the frequency spectrum includes a spectrum equal to or greater than a second threshold value, and judges that the pulse detector is in an unworn state in the case that the frequency spectrum does not include a spectrum equal to or greater than a second threshold value, when the unworn-state detector has judged the state to be an unworn state and judged at a predetermined length of time prior that the state is an unworn state.

In the present aspect, an example of judgment that the unworn state has ended is made apparent. When the state has been judged to be an unworn state by the previous detection process and the state has been judged to be a non-unworn state by the current detection process in aspects (3) and (4) described above, it is highly possible that an immediate judgment that the unworn state has ended (a change for an unworn state to a worn state) will be an incorrect judgment. For example, in a state in which the pulse detector is left unworn on a desk, there can be cases in which the intensity of the light incident on the pulse wave sensor is accidently made to fluctuate due to a person passing nearby, and the state of the pulse wave signal enters a state similar to a signal state that occurs when the pulse detector has been worn by the subject.

In view of the above, in the present aspect, a temporary judgment is made that the state is an unworn state, and when a non-unworn state (worn state) is subsequently judged, the unworn-state detector makes a further judgment using additional conditions. In other words, it is examined whether the frequency spectrum obtained as a result of the frequency analysis of the pulse wave signal includes a spectrum equal to or greater (in magnitude) than a second threshold value, and if the frequency spectrum includes such a spectrum, it is judged that the state is a non-unworn state, and if the frequency spectrum does not include such a spectrum, it is judged that the state is an unworn state.

In the present aspect, the conditions are weighted and judgment is made with greater care when a judgment is made as to whether the unworn state has ended. Therefore, the possibility of an errant judgment is reduced.

(6) In another aspect of the pulse detector of the invention, the unworn-state detector performs a detection of the unworn state at predetermined time intervals; and, when the unworn state of the pulse detector has been detected by the current detection process, discards at least one among the past frequency analysis results of the pulse wave signal, and information showing a trend of the frequency of the pulse signal used in the frequency analysis of the pulse wave signal.

The pulse signal is detected on the basis of past frequency analysis results, past frequency trends in the pulse signal, and other factors. Therefore, when the pulse signal has been mistakenly detected, it is possible that the detection process will be continued thereafter according to the noise component.

In view of the above, in the present aspect, the unworn-state detector discards at least one among the past frequency analysis results of a pulse wave signal, and information showing a trend of the frequency of the pulse signal used in the frequency analysis of the pulse wave signal, when the unworn-state detector has detected that the pulse detector is in an unworn state by the current detection. In the case that the unworn pulse detector has again been worn by the subject, the pulse detector can start pulse detection processing from, e.g., an initial state. Therefore, the pulse signal can be accurately detected.

(7) In another aspect of the pulse detector of the invention, the pulse detector has a subject information acquisition section for acquiring at least one of biological information of the subject and accompanying information related to activity by the subject; and the unworn-state detector stops operation of the subject information acquisition section when the unworn state has been detected.

Power consumption is increased when the process for displaying (notification to the subject) the pulsation count (biological information of the subject) or the like, and the burned calories (accompanying information related to activity by the subject) or the like is continued even though the pulse detector is in an unworn state.

In view of the above, in the present aspect, the unworn-state detector stops operation of the subject information acquisition section (having a function for acquiring at least one of biological information of the subject and accompanying information related to activity by the subject) when the unworn state of the pulse detector has been detected. Accordingly, wasteful power consumption does not occur. Display (broadly defined notification) of errant information can also be prevented.

The phrase "stops operation of the subject information acquisition section" includes, e.g., not performing operation for acquiring information or preventing the operation itself by switching off the power of the subject information acquisition section. Switching off the power produces a greater effect of reducing power consumption.

(8) In another aspect of the pulse detector of the invention, the unworn-state detector stops the frequency analysis operation carried out by the frequency analyzer when the unworn state has been detected.

When the pulse detector is in an unworn state, a significant frequency spectrum cannot be obtained when frequency analysis is carried out. In view of this fact, in the present aspect, the unworn-state detector stops the frequency analysis operation carried out by the frequency analyzer when the pulse detector is detected to be in an unworn state. Accordingly, wasteful power consumption does not occur. Display (broadly defined notification) of errant information can also be prevented. The phrase "stops a frequency analysis operation of the frequency analyzer" includes, e.g., not performing the frequency analysis process, or preventing the operation itself by switching off the power of the portion of the frequency analyzer that carries out the frequency analysis process. Switching off the power produces a greater effect of reducing power consumption.

In this manner, in accordance with at least one aspect of the invention, it is possible to detect that, e.g., the pulse detector is in an unworn state. For example, the unworn state of the pulse detector can be detected with high accuracy without the use of a special configuration.

BRIEF DESCRIPTION OF THE DRAWINGS

Referring now to the attached drawings which form a part of this original disclosure.

DETAILED DESCRIPTION OF EXEMPLARY EMBODIMENTS

The invention is described in detail below with reference to the drawings. The present embodiment described below is not unreasonably limited to the details of the invention described in the claims. The entire configuration described in the present embodiment is not necessarily the essential constituent feature of the invention.

First Embodiment

Figure 1:
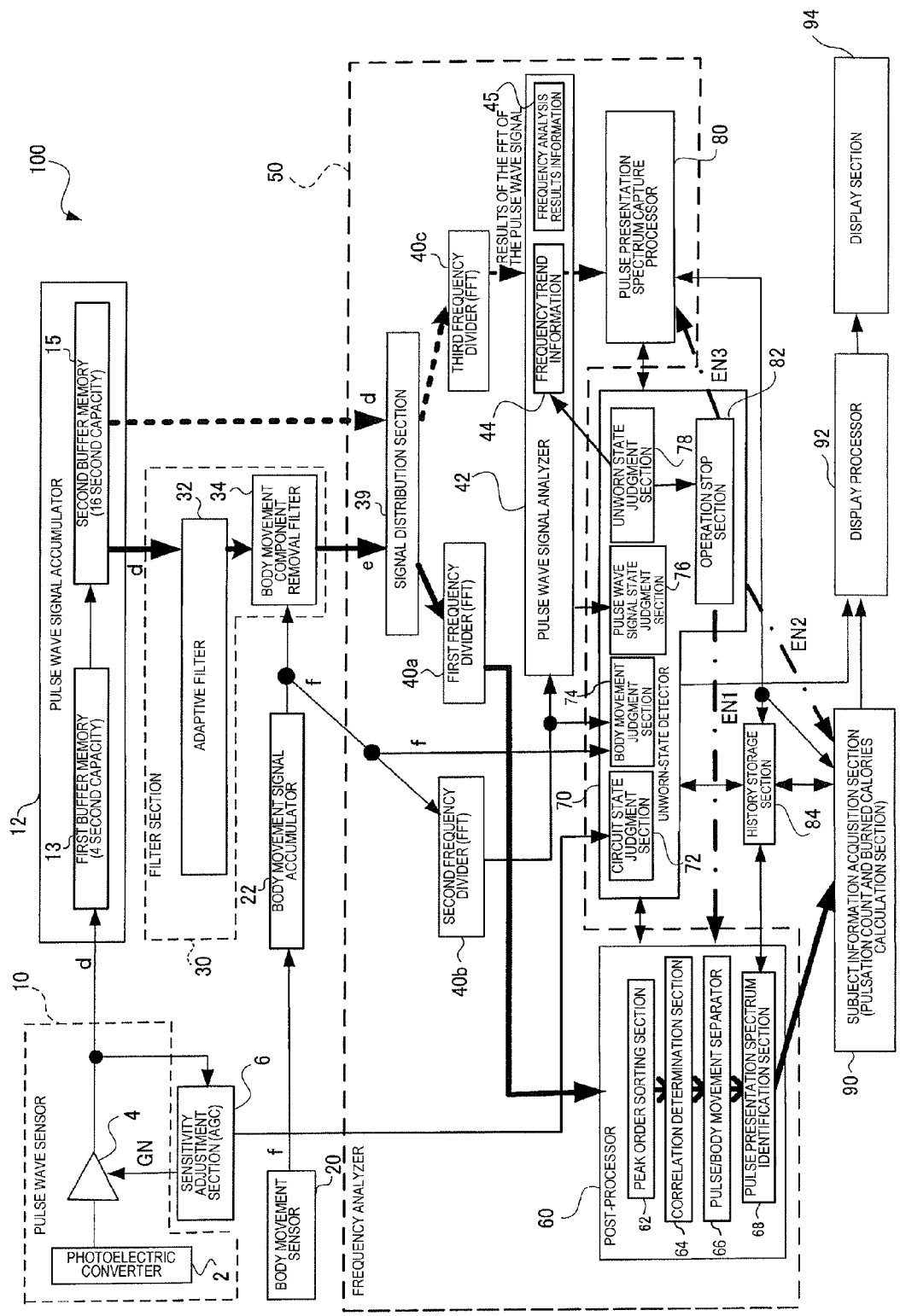
FIG. 1 is a view showing the configuration of an example of the pulse detector of the invention.

FIG. 1 is a view showing the configuration of an example of the pulse detector of the invention. The pulse detector 100 shown in FIG. 1 is a type of sensor device for detecting a pulse signal that originates in the pulse of a subject (including humans and animals), and a heartbeat and other biological information and the like that correspond to a pulse signal.

Here, the word "pulse" in medical terms refers to activity that occurs when periodic contractions and relaxations of the heart as well as internal organs in general are repeated. As used herein, the term "pulse" refers to pumping motion by which the heart periodically sends blood. A heart rate is referred to as the number of pulses of the heart in a single minute. The pulsation count is the number of throbs in a peripheral blood vessel. This number of times thus counted shall be referred to as a "pulsation count" or merely as a "pulsation" because pulsations occur in the arteries when the heart sends blood out. In medical terms, the measurement of throbs in the arm is ordinarily referred to as pulsation count rather than heart rate. Also, in the description below, the term "body movement" is used.

As used herein, the term "body movement" shall widely refer to all body movements. A body movement sensor signal is a signal that originates in this widely defined body movement. The body movement sensor signal includes a body movement signal (corresponding to constant noise), which is a signal component that accompanies periodic body movement of the subject. The term "body movement" in relation to the body movement signal (or bode movement component) is narrowly defined as body movement that refers to "periodic body movement." The periodic body movement of the subject is periodic, i.e., constant arm motion or the like that accompanies, e.g., walking, jogging, and the like.

Overall Configuration

The pulse detector 100 shown in FIG. 1 has a pulse wave sensor 10 that outputs a pulse wave signal d, which possibly includes a pulse signal, and at least one constant noise having periodicity and non-constant noise that does not have periodicity; a pulse wave sensor sensitivity adjustment section 6, a pulse wave signal accumulator (having a first buffer memory 13 for accumulating four seconds of pulse wave signal d data, and a second buffer memory 15 for accumulating 16 seconds of pulse wave signal d data) 12; a filter section 30 that includes an adaptive filter 32 and a body movement component removal filter 34; a body movement sensor (an acceleration sensor, gyro sensor, or the like) 20; a body movement sensor signal accumulator 22; a frequency analyzer 50; an unworn-state detector 70 (including a circuit state judgment section 72, a body movement judgment section 74, a pulse wave signal state judgment section 76, an unworn-state judgment section 78, and an operation stop section 82); a history storage section 84; a subject information acquisition section (pulsation count and burned-calorie calculation section) 90; a display processor 92, and a display section 94.

The frequency analyzer 50 has a signal distribution section 39, a first frequency divider 40a, a second frequency divider 40b, a third frequency divider 40c, a pulse wave signal analyzer 42 that accumulates frequency trend information 44, a post-processor 60 (including a peak order sorting section 62, a correlation determination section 64, a pulse/body movement separator 66, and a pulse presentation spectrum identifier 68), and a pulse presentation spectrum capture processor 80.

The pulse wave sensor 10 is a pulse wave sensor based on, e.g., a photoelectric pulse wave sensor and the principles thereof. The pulse wave sensor 10 outputs the pulse wave signal d, which possibly includes a pulse signal. The pulse wave sensor 10 has an LED or another light source (not shown in FIG. 1); a photoelectric converter 2 that receives and converts to an electric signal reflected light that is generated when the output light of the light source is reflected by blood vessels (not shown in FIG. 1) as a source of biological information; and an amplifier (variable gain amplifier) 4 that amplifies the output signal of the photoelectric converter 2. The sensitivity of the pulse wave sensor 10 is examined by the amplification factor (gain) of the amplifier 4. The gain of the amplifier 4, i.e., the sensitivity of the pulse wave sensor 10 can be adjusted by the pulse wave sensor sensitivity adjustment section 6. The pulse wave sensor sensitivity adjustment section 6 is composed of, e.g., an automatic gain control circuit (AGC circuit) that automatically adjusts amplifier gain. In the description below, the pulse wave sensor sensitivity adjustment section 6 can be merely referred to as the sensitivity adjustment section 6.

The sensitivity adjustment section 6 adjusts the sensitivity of the pulse wave sensor 10 (i.e., the gain of the amplifier 4) on the basis of the intensity (level) of the input signal to the pulse wave sensor 10 or pulse wave signal d. In the case that, e.g., the sensitivity of the pulse wave sensor 10 (the gain of the amplifier 4) is adjusted on the basis of intensity (level) of the input signal to the pulse wave sensor 10, the sensitivity adjustment section 6 can adjust (control) the sensitivity of the pulse wave sensor 10 (the gain of the amplifier 4) so that the level of the pulse wave signal d arrives at a predetermined level (feedforward scheme). In the case that, e.g., the sensitivity of the pulse wave sensor 10 (the gain of the amplifier 4) is adjusted on the basis of intensity (level) of the pulse wave signal d outputted from the pulse wave sensor 10, the sensitivity adjustment section 6 can adjust (control) the sensitivity of the pulse wave sensor 10 (the gain of the amplifier 4) so that the level of the pulse wave signal d arrives at a predetermined level (feedback scheme). Described below is an example in which a feedback scheme circuit (AGC circuit) is used.

The body movement sensor 20 detects the body movement of the subject and outputs a body movement sensor signal f that originates from body movement.

Four seconds of the pulse wave signal d outputted from the pulse wave sensor 10 is accumulated in the first buffer memory 13. The four seconds of the pulse wave signal d is transferred to the second buffer memory 15 in four-second cycles. The second buffer memory 15 is first-in, first-out (FIFO) memory, and 16 seconds of the pulse wave signal is updated in four-second segments. The reason that 16 seconds of the pulse wave signal is accumulated is that changes in the signal must be observed for a certain length of time to carefully evaluate the existence or the like of a correlation when the pulse component is to be identified by frequency analysis.

The filter section 30 minimizes the noise included in the input signal. The signal, component that is included in the pulse wave signal d and that originates in body movement is minimized by the body movement component removal filter 34.

The frequency analyzer 50 performs a frequency analysis at predetermined time intervals (e.g., every four seconds) on the basis of the pulse wave signal d or a filtered signal e obtained by filtering (by the filter section 30) the pulse wave signal d to suppress noise included in the pulse wave signal. It is furthermore possible to identify the pulse presentation spectrum that shows the pulse signal.

The signal distribution section 39 feeds the filtered signal e to the first frequency divider (fast Fourier transform section (FFT)) 40a and feeds the pre-filtered pulse wave signal d to the third frequency divider 40c. The body movement sensor signal f is fed to the second frequency divider 40b.

The post-processor 60 has a peak order sorting section 62 for sorting the frequency spectrum in the order of the magnitude of the spectrum values; a correlation determination section 64 for determining a correlation between the higher peak order main spectrum and the spectrum of the most recent past pulse signal; a pulse/noise separator 66 for separating the pulse signal and the noise component using the results of the correlation determination; and a pulse presentation spectrum identifier 68 for identifying as the pulse presentation spectrum the spectrum of the pulse component separated from the noise by the pulse/noise separation process.

When the pulse presentation spectrum has been successfully identified, the subject information acquisition section (pulsation count and burned-calorie calculation section) 90 calculates at least one of the pulsation count, which is biological information of the subject, and the burned calories, which is accompanying information related to activity by the subject. The pulsation count is calculated on the basis of, e.g., the frequency of the pulse presentation spectrum. The burned calories are calculated on the basis of the pulsation count.

The subject information (at least one of the pulsation count and burned calories) thus calculated is fed from the subject information acquisition section (pulsation count and burned-calorie calculation section) 90 to the display section 94 by way of the display processor 92. As a result, a numerical value showing, e.g., the pulsation count and burned calories is displayed by the display section 94. It is also possible to display variation of detected throbs rather than the pulsation count on the time axis in the form of a signal waveform or a graph (broadly defined notification).

The pulse presentation spectrum capture processor 80 included in the frequency analyzer 50 preferably starts operation when, e.g., the post-processor 60 has failed to identify the pulse presentation spectrum based on the filtered signal e. The pulse presentation spectrum capture processor 80 attempts to capture the pulse presentation spectrum by making a correlation determination that is based, e.g., on the frequency trend of past pulse signals, on the basis of the pre-filtered pulse wave signal d (having a larger signal value than the filtered signal because the signal is not attenuated by filtering).

The pulse wave signal analyzer 42 analyzes the frequency spectrum of the pulse wave signal d, evaluates the signal state of the pulse wave signal d, and acquires the frequency trend information 44 of the pulse presentation spectrum that shows the pulse signal, and frequency analysis result information 45. The signal state of the pulse wave signal d is evaluated on the basis of, e.g., the amount of noise in the pulse wave signal d (which can be the clarity of the pulse wave signal d). The amount of noise in the pulse wave signal d can be evaluated using an evaluation index. The evaluation index can be the ratio of spectrum values of the main frequency spectrum (e.g., later-described indexes referred to as r5, r10), or statistical information (statistical index) such as the standard deviation and deviation value.

The unworn-state detector 70 detects whether the pulse detector 100 is in an unworn state of having been removed from the subject, on the basis of the sensitivity (gain value) of the pulse wave sensor 10 adjusted by the sensitivity adjustment section 6 and the body movement sensor signal f outputted from the body movement sensor 20.

The unworn-state detector 70 includes the circuit state judgment section 72, the body movement judgment section 74, the pulse wave signal state judgment section 76, the unworn-state judgment section 78, and the operation stop section 82.

The circuit state judgment section 72 judges the circuit state (here, the state of the amplifier 4 included in the pulse wave sensor 10) on the basis of the sensitivity (gain value) information adjusted by the sensitivity adjustment section 6.

The body movement judgment section 74 judges whether the signal value of the body movement sensor signal f is sufficiently large to allow judgment that there is body movement.

The pulse wave signal state judgment section 76 judges whether there is a significant spectrum in the pulse wave signal d that has a signal value equal to or greater than a predetermined threshold value (in this case, the first threshold value). The pulse wave signal state judgment section 76 also judges the amount of noise (e.g., low noise, intermediate, noisy) in the pulse wave signal d with reference to, e.g., the analysis results of the pulse wave signal analyzer 42.

The unworn-state judgment section 78 examines, e.g., whether conditions for judging the unworn state are satisfied and judges the unworn state/non-unworn state (worn state).

The operation stop section 82 preferably discards (e.g., initializes) past frequency trend information 44 when the pulse detector 100 has been judged to be in an unworn state by the unworn-state judgment section 78. Also, the identification process of the pulse presentation spectrum carried out by the post-processor 60 and the pulse presentation spectrum capture process carried out by the pulse presentation spectrum capture processor 80 can be stopped. Also, the subject information (pulsation count and burned calories) calculation process carried out by the subject information acquisition section (pulsation count and burned-calorie calculation section) 90 can be stopped.

Frequency information about the identified or captured pulse presentation spectrum, information showing the unworn/non-unworn state, and calculated subject information (pulsation count and burned calories) are chronologically stored in the history storage section 84. The stored information can be referenced as required by each section.

Operation and the Like of the Unworn-State Detector

As described above, the unworn-state detector 70 detects the unworn state of the pulse detector 100 on the basis of the sensitivity (GN) of the pulse wave sensor 10, which is information showing the circuit state, adjusted by the pulse wave sensor sensitivity adjustment section 6, and the body movement sensor signal f outputted from the body movement sensor 20.

Figure 2A:
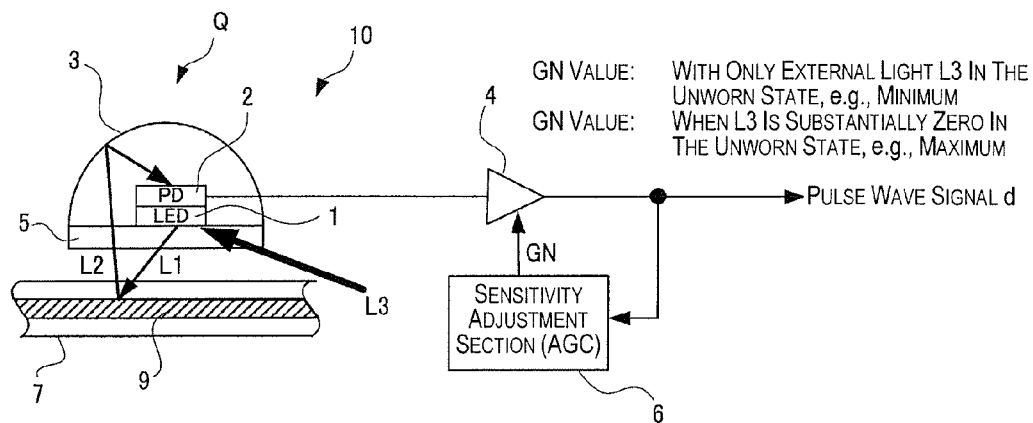
FIGS. 2A and 2B are views for describing the operation for adjusting the sensitivity of the pulse wave sensor.
Figure 2B:
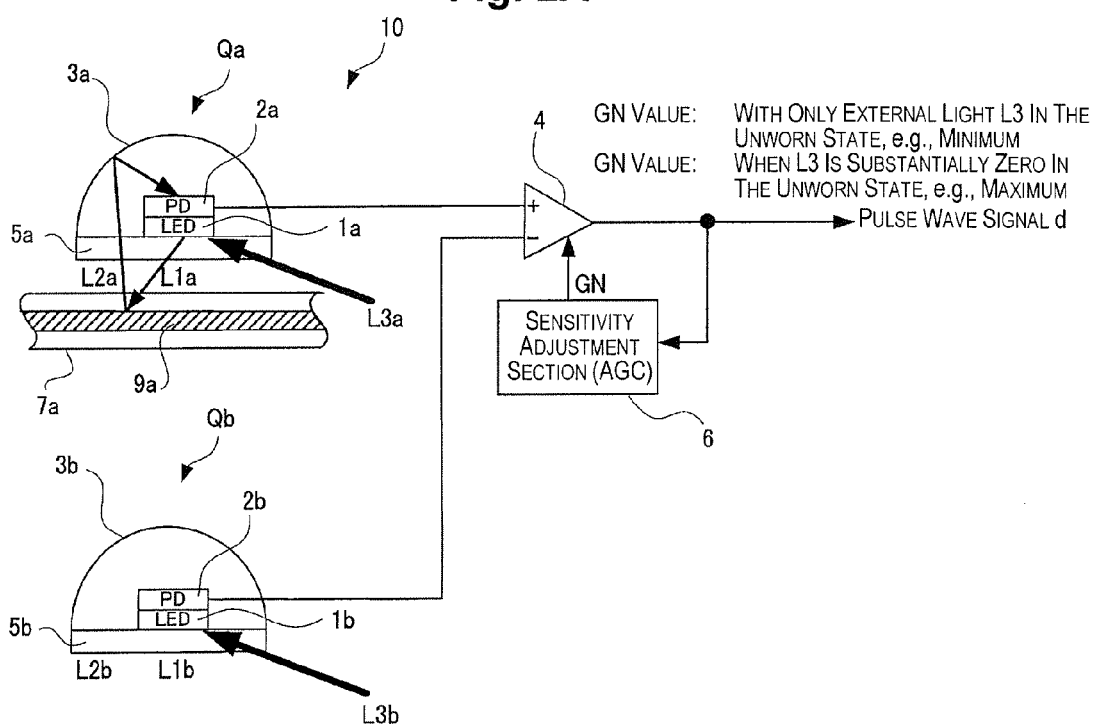

Here, reference will be made to FIGS. 2A and 2B. FIGS. 2A and 2B are views for describing the operation for adjusting the sensitivity of the pulse wave sensor. FIG. 2A shows a single-type pulse wave sensor, and FIG. 2B shows a twin-type pulse wave sensor.

First, the single-type pulse wave sensor 10 shown in FIG. 2A will be described. The single-type pulse wave sensor 10 is a pulse wave sensor of type that uses a single sensor structure Q.

The sensor structure Q included in the single-type pulse wave sensor 10 has, e.g., an LED or another light source 1, a photoelectric converter (photodiode (PD)) 2 that receives and converts to an electric signal reflected light L2 that is generated when output light L1 of the light source 1 is reflected by blood vessels (biological information source) 9 in a predetermined location (wrist, finger, or the like) 7 of the subject; a dome-shaped reflective surface 3, and an optically transparent substrate (e.g., a glass substrate) 5.

The output signal of the photoelectric converter (PD) 2 is amplified by an amplifier (e.g., variable gain amplifier) 4. The sensitivity GN of the pulse wave sensor 10 is examined by the amplification factor (gain) of the amplifier 4. The gain of the amplifier 4, i.e., the sensitivity GN of the pulse wave sensor 10 is adjusted by the pulse wave sensor sensitivity adjustment section (sensitivity adjustment section) 6. The sensitivity adjustment section 6 is composed of, e.g., an AGC circuit (automatic gain control circuit) that automatically adjusts the gain GN of the amplifier 4. The sensitivity adjustment section 6 automatically adjusts the gain GN of the amplifier 4 so that the level of the pulse wave signal d, which is an output signal of the pulse wave sensor 10, becomes a predetermined level (e.g., a fixed level).

In a state in which the pulse detector 100 is worn by the subject and the pulse detection process is being carried out, the sensitivity (GN) adjusted (set) by the sensitivity adjustment section 6 is a value in a range that corresponds to the magnitude of the electric signal generated when the reflected light L2 from the blood vessels 9 is received.

In contrast, in the case that the pulse detector 100 is removed from the subject and is in an unworn state, the sensitivity is highly likely to be a value outside of the range (permissible range) generated during ordinary measurement.

In other words, when, e.g., the pulse detector 100 is left unworn on a desk, there can be cases in which light from indoor lighting or outdoor light that enters through a window or the like (these will be generically referred to as external light L3) will be incident on the pulse wave sensor. The external light L3 is directly incident on the pulse detector, but the light used for pulse detection is the reflected light L2 (which can be scattered light, or indirectly incident light) reflected by blood vessels. Therefore, the level of the external light L3, which is direct light, can be greater than the level of the reflected light L2 used for pulse detection. In this case, it is possible that the gain of the amplifier 4 (the sensitivity GN of the pulse wave sensor 10) is adjusted to be a sufficiently small value, e.g., adjusted to be near the minimum gain so that the level of the pulse wave signal d does not become excessively high.

In the case that the pulse detector 100 is, e.g., stored away in a desk drawer or a bag, the level of external light L3 is near zero because the external light L3 is substantially blocked off. In other words, the state in this case is such that the level of external light is sufficiently lower than the level of the reflected light used for pulse detection. In this case, there is a possibility that the gain of the amplifier 4 (the sensitivity GN of the pulse wave sensor 10) is adjusted to be a sufficiently large value, e.g., adjusted to be near maximum gain in order to bring the level of the pulse wave signal d to a predetermined level.

In other words, when the pulse detector is in an unworn state, it is possible that the intensity of the light (the light level) incident on the pulse wave sensor will be an intensity (level) in an impossible range during ordinary detection processing. At this time, the sensitivity (GN) is also a value outside of the range (permissible range) generated during ordinary measurement. Therefore, the sensitivity of the pulse wave sensor set by the pulse wave sensor sensitivity adjustment section can be used as effective information for detecting the unworn state of the pulse detector.

Next, the twin-type pulse wave sensor shown in FIG. 2B will be described. In accordance with a twin-type pulse wave sensor, the effect of removing the effect of outside light can be obtained. In a twin-type pulse wave sensor, two sensor structures Q shown in FIG. 2A are used.

The sensor structures Qa, Qb in the twin-type pulse wave sensor 10 shown in FIG. 2B have the same structure as the sensor shown in FIG. 2A, and the same reference numerals are used for the same constituent elements. However, the letters a and b are added to the reference numerals because it is necessary to distinguish between the two sensor structures (first sensor structure Qa, second sensor structure Qb). The second sensor structure Qb is not required to have an LED 1b.

In the twin-type pulse wave sensor 10 of FIG. 2B, the reflected light L2a from the surface of the blood vessels 9a is received by only the first sensor structure Qa. The second sensor structure Qb receives only external light L3b. In the pulse wave sensor shown in FIG. 2B, a differential amplifier is used as the amplifier 4. The output signal of the first sensor structure Qa and the output signal of the second sensor structure Qb are inputted to the input terminals of the amplifier 4. At this point, the noise component included in the input signals that corresponds to the external light L3 is offset and removed.

Consider the case in which considerably strong external lights L3a, L3b are incident on the first sensor structure Qa and second sensor structure Qb when the pulse detector 100 is, e.g., left unworn on a desk. In this case, the level of the pulse wave signal d outputted from the amplifier (differential amplifier) 4 is essentially zero due to the effect of offsetting the external light component by the differential configuration. Therefore, the sensitivity adjustment section 6 attempts to increase the level of the pulse wave signal d, and as a result, there is a high possibility that the gain of the amplifier 4 (GN of the pulse wave sensor 10) will be adjusted to a sufficiently high value, e.g., adjusted to near maximum gain. The same applies to when the pulse detector 100 is, e.g., left unworn in a desk drawer or in a bag (when the level of the external light L3 is near zero). In other words, the level of the pulse wave signal d becomes essentially zero due to the effect of offsetting the external light component by the differential configuration. Therefore, the sensitivity adjustment section 6 attempts to increase the level of the pulse wave signal d, and as a result, there is a high possibility that the gain of the amplifier 4 (the sensitivity of the pulse wave sensor 10) will be adjusted to a sufficiently high value, e.g., adjusted to near maximum gain.

In this manner, when the pulse detector is in an unworn state, there is a high possibility that the sensitivity (GN) of the pulse wave sensor 10 will be a value outside of the range (permissible range) generated during ordinary measurement, and therefore, the sensitivity (GN) of the pulse wave sensor 10 set by the sensitivity adjustment section 6 can be used as effective information for detecting the unworn state of the pulse detector.

Here, consider the case in which the external light L3 varies for some reason and noise is outputted from the photoelectric converter PD when the sensitivity (GN) of the pulse wave sensor is, e.g., a near-maximum value. In this case, a fairly high noise component is included in the pulse wave signal d because the noise is amplified by the amplifier 4 at high gain.

When the pulse wave signal d is analyzed by the pulse wave signal analyzer 42 included in the frequency analyzer 50, it is difficult to make a sharp distinction between the noise and the pulse signal in the case that, e.g., a frequency component similar to past pulse signals is included by chance in the pulse wave signal d.

Figure 3:
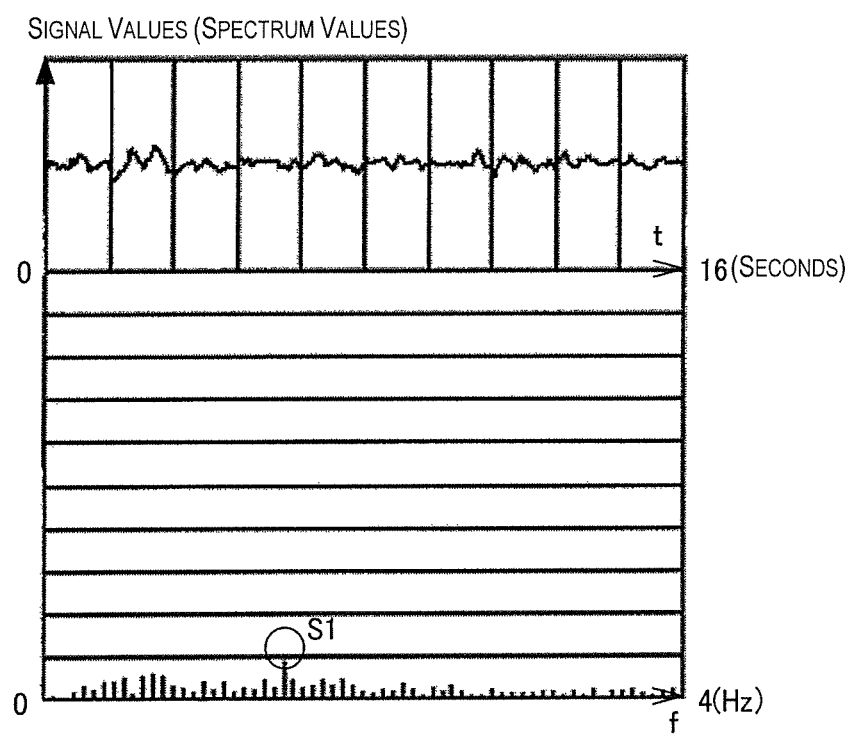
FIG. 3 is a view showing an example of the frequency spectrum of a pulse wave signal that contains a large number of noise components.

FIG. 3 is a view showing an example of a pulse wave signal and frequency spectrum in the case that the pulse detector has been removed from the subject and left unworn on a desk while pulse detection processing is being carried out. The signal waveform of 16 seconds of the pulse wave signal d prior to FFT is shown in the upper side of FIG. 3. The horizontal axis represents time and the vertical axis represents signal amplitude. The frequency spectrum in the frequency band 0 to 4 Hz is shown in the lower side. The horizontal axis represents the frequency and the vertical axis represents the signal value (spectrum value).

In FIG. 3, the frequency spectrum S1 is a spectrum of a frequency component that is similar to a past pulse signal and that is inside the noise component. In the present embodiment, the unworn-state detector 70 detects that the pulse detector is in an unworn state, and, e.g., the operation stop section 82 stops the operation of the post-processor 60. Therefore, the frequency spectrum S1 in FIG. 3 is not judged to be the pulse presentation spectrum.

Also, when the pulse detector 100 is in an unworn state, there is a high possibility that the level of the body movement sensor signal (the signal that originates in subject body movement) outputted from the body movement sensor 20 is a level within range that can be considered to be zero (because there is no body movement).

Therefore, in the present embodiment, the unworn-state detector 70 judges the unworn state of the pulse detector 100 on the basis of the sensitivity of the pulse wave sensor 10 (the value of the sensitivity GN) and the body movement sensor signal f. For example, the unworn-state detector 70 can judge that the pulse detector 100 is in an unworn state when the sensitivity is a value outside the range (permissible range) generated during ordinary measurement and the level of the body movement sensor signal f is a level within a range that can be considered to be zero (i.e., a level at which body movement can be assumed to be nonexistent).

It is possible to judge whether the level of the body movement sensor signal f is a level within a range that can be considered to be zero, on the basis of the signal value of the body movement sensor signal f prior to frequency analysis (FFT), or on the basis of the frequency spectrum obtained by frequency analysis (FFT) of the body movement sensor signal f. For example, if the subject is performing periodic activity, a large spectrum that corresponds to the body movement signal appears in the frequency spectrum obtained as a result of FFT.

In this manner, the unworn-state detector 70 of the present embodiment can judge the unworn state with high accuracy because reference is made to the sensitivity of the pulse wave sensor 10 adjusted by the pulse wave sensor sensitivity adjustment section 6, the sensitivity being information that shows the state of the circuit; and because dual use is furthermore made of the magnitude information of the body movement sensor signal f to judge the unworn state. The structure of the pulse detector 100 is not made more complex because a special configuration is not used (a configuration for detecting a pressing force on the device main body, or for detecting ground potential). Also, the pulse detector 100 can be made smaller and a pulse detector 100 having high utility can be obtained.

In addition to referencing the sensitivity of the pulse wave sensor 10 and the magnitude of the body movement sensor signal f, the unworn-state detector 70 can furthermore judge the unworn state of the pulse detector 100 by referencing the results of the frequency analysis of the pulse wave signal d carried out by the frequency analyzer 50 (specifically, the pulse wave signal analyzer 42). The precision of unworn detection is thereby improved. Judgment of the possibility of an unworn state based on the results of the frequency analysis of the pulse wave signal d carried out by the pulse wave signal analyzer 42 is carried out by, e.g., the pulse wave signal state judgment section 76 included in the unworn-state detector 70.

When the pulse detector 100 is worn by the subject and, e.g., the subject is in a state of constant activity, there is a high possibility that a pulse signal that originates in the pulse of the subject and a signal component that originates in the body movement of the subject will be included in the pulse wave signal d outputted from the pulse wave sensor 10.

When the frequency spectrum is analyzed by frequency analysis of the pulse wave signal d, a signal having periodicity appears in a specific frequency position on the frequency axis. Therefore, when a frequency spectrum having a greater signal value than a predetermined threshold value (herein referred to as the first threshold value) is present, the pulse wave signal state judgment section 76 judges that the pulse detector 100 is in a non-unworn state.

A frequency spectrum in which a pulse signal with a high signal value and a body movement sensor signal with a large signal value are both present appears when, e.g., the subject is in a state of constant (periodic) activity (e.g., a state in which the subject is walking with a fixed pitch while regularly swinging the arms). In other words, a large body movement sensor signal is observed because a characteristic body movement signal that originates in the constant activity of the subject is included in the body movement sensor signal of this case. Therefore, the pulse wave signal state judgment section 76 judges that the pulse detector 100 is in a non-unworn state when a frequency spectrum having a plurality of signals with signal values that are greater than the first threshold value has appeared.

On the other hand, the frequency spectrum obtained as a result of a frequency analysis of the pulse wave signal d is compared with the first threshold value, and as a result, the pulse wave signal state judgment section 76 judges that the pulse detector 100 is in an unworn state in the case that there is no spectrum in which the signal value exceeds the predetermined threshold value, i.e., when there is no spectrum (significant spectrum) having valid information about pulse or state of activity of the subject.

In this manner, the precision of judging the unworn state/non-unworn state by the unworn-state judgment section 78 can be improved by having the frequency analyzer 50 (specifically, the pulse wave signal analyzer 42) judge the unworn state with additional reference to the results of the frequency analysis of the pulse wave signal.

The unworn-state judgment section 78 included in the unworn-state detector 70 comprehensively judges the unworn/non-unworn state of the pulse detector 100 from the viewpoint of whether the above-described plurality of conditions have been met.

For example, the unworn-state detector 70 can judge that the pulse detector 100 is in an unworn state in the case that: the sensitivity of the pulse wave sensor 10 is a value outside a possible permissible range when the pulse signal is detected; the level of the body movement sensor signal f outputted from the body movement sensor 20 is within a range judged to be devoid of subject body movement; and there is no spectrum equal to or greater than the first threshold value in the frequency spectrum obtained as a result of frequency analysis of the pulse wave signal d. In this case, the unworn state of the pulse detector 100 can be detected with high accuracy without the use of a special configuration When an unworn state of the pulse detector 100 is to be detected, the above-stated condition that "a spectrum equal to or greater than a first threshold value does not exist in the frequency spectrum obtained as a result of frequency analysis of the pulse wave signal" can be substituted by the condition stated as "an amount of noise in the pulse wave signal is classified as intermediate or noisy on the basis of the frequency spectrum obtained as a result of frequency analysis of the pulse wave signal where, e.g., the amount of noise is classified as low, intermediate, or noisy."

The case in which the amount of noise in the pulse wave signal d is judged to be "low noise" corresponds to when, e.g., the subject is in a state of constant (periodic) activity (e.g., walking while regularly swinging the arms).

The case in which the amount of noise in the pulse wave signal d is judged to be "intermediate (moderate)" corresponds to when the subject is constantly active (e.g., walking while regularly swinging the arms) and is also moving the wrist in an irregular fashion or performing another aperiodic activity. The frequency spectrum in such a case is a spectrum such as when "there exists both a pulse signal and a body movement sensor signal having a higher signal value than a predetermined threshold value, and external noise is furthermore present across a wide range on the frequency axis."

The case in which the amount of noise in the pulse wave signal d is judged to be "noisy" corresponds to when, e.g., the subject is doing irregular exercise, or playing basketball or the like. In this case, external noise having a signal value that exceeds a predetermined threshold value for judging external noise often appears, e.g., in a wide range of positions on the frequency axis in the frequency spectrum of the pulse wave signal.

Figure 4:
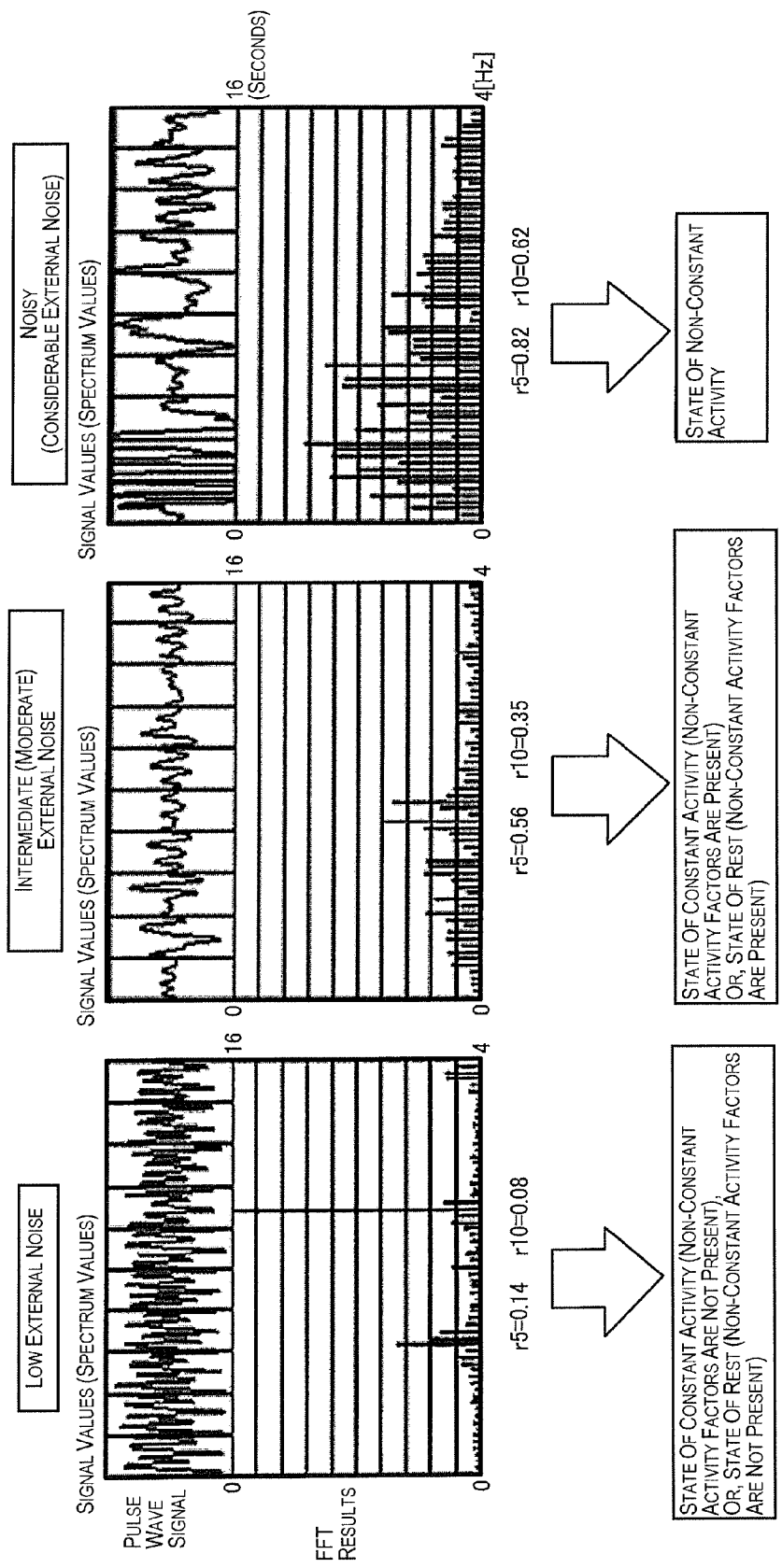
FIGS. 4A to 4C are views showing evaluation examples of the amount of noise in a pulse wave signal in view of the external noise included in the pulse wave signal, and evaluation examples of activity states that correspond to the evaluation examples.

The relationship between the evaluation of the amount of noise in the pulse wave signal d and the state of activity of the subject will be described later with reference to FIG. 4.

Among the three classifications described above, there is a very high possibility that the pulse detector 100 is being worn rather than unworn by the subject at least when the state of the pulse wave signal is "low noise." However, it is also possible to envision "a case in which the pulse detector 100 is in an unworn state and a considerable amount of noise is generated for some reason" as a case in which the state of the pulse wave signal d is "intermediate" or "noisy."

Therefore, the unworn-state detector 70 preferably judges that the pulse detector 100 is in the unworn state in the case that the sensitivity (GN) of the pulse wave sensor 10 is a value outside a possible permissible range when the pulse signal is detected; the level of the body movement sensor signal f outputted from the body movement sensor is within a range judged to be devoid of body movement of the subject; and the amount of noise in the pulse wave signal is classified as intermediate or noisy. The amount of noise in the pulse wave signal d can be judged using as an index, e.g., a ratio of the signal values of two spectrums selected from among the main spectrum, or can be statistical information (standard deviation, deviation value, or the like).

The unworn/non-unworn state is judged with consideration given also to the signal state of the pulse wave signal d, whereby the unworn state of the pulse detector can be detected with higher accuracy without the use of a special configuration. The unworn-state detector 70 can differentiate between when the subject is, e.g., in a resting state (no constant activity factors) and when the pulse detector is in an unworn state.

Here, reference will be made to FIGS. 4A to 4C. FIGS. 4A to 4C are views showing evaluation examples of the amount of noise in a pulse wave signal in view of the external noise included in the pulse wave signal, and evaluation examples of activity states that correspond to the evaluation examples.

In FIGS. 4A to 4C, the signal waveform of 16 seconds of the pulse wave signal d prior to FFT is shown in the upper side. The horizontal axis represents time and the vertical axis represents signal amplitude. The frequency spectrum in the frequency band 0 to 4 Hz is shown in the lower side. The horizontal axis represents the frequency and the vertical axis represents the spectrum values.

The amount of noise of the pulse wave signal can be evaluated using an evaluation index. For example, a spectrum ratio is calculated and used as an evaluation index, the spectrum ratio being a ratio of spectrum values of a first spectrum showing the maximum spectrum value among the frequency spectrums obtained by frequency analysis of the pulse wave signal d, and at least a second spectrum other than the first spectrum.

In the examples in FIGS. 4A to 4C, a ratio of the spectrum values (the ratio of baseline heights) of the main frequency spectrum is used as the index for estimating the amount of external noise. Specifically, indexes referred to as $r5$ and $r10$ are used (however, this is an example, and it is also possible to use another statistical index, e.g., standard deviation or the like). Here, $r5$ is an index obtained using the spectrum value (power) of the first spectrum as the denominator and using the spectrum value (power) of the fifth spectrum as the numerator, where five spectrums from among the frequency spectrums of 16 seconds of pulse wave signal have been arranged (i.e., when sorted) in order of the magnitude of the peak values.

Also, $r10$ is an index obtained using the spectrum value (power) of the first spectrum as the denominator and using the spectrum value (power) of the tenth spectrum as the numerator, where 10 spectrums from among the frequency spectrums of 16 seconds of pulse wave signal have been arranged (i.e., when sorted) in order of the magnitude of the peak values. The indexes $r5$ and $r10$ are acquired by, e.g., the pulse wave signal analyzer 42.

The pulse wave signal analyzer 42 calculates the indexes $r5$ and $r10$ on the basis of the results of the frequency analysis of the pulse wave signal d, compares the indexes $r5$ and $r10$ with a predetermined threshold value, uses the comparison results to evaluate the amount of noise in the pulse wave signal d, and ascertains the state of the pulse wave signal d as a result of the evaluation, as shown in FIGS. 4A to 4C.

Here, as an example, low noise (the level of clarity of the pulse wave signal is high) is defined as $r5<0.5$ and $r10<0.2$, high noise (noisy) is defined as $r5>0.7$ and $r10>0.5$, and intermediate (moderate) noise is defined as being neither of the above.

The example of FIG. 4A is judged to have low external noise (clear) because $r5=0.14$ and $r10=0.08$. The example of FIG. 4B is judged to have intermediate (moderate) external noise because $r5=0.56$ and $r10=0.35$. The example of FIG. 4C is judged to have high external noise (noisy) because $r5=0.82$ and $r10=0.62$.

The waveform of the pulse wave signal d and the frequency spectrum are in a close relationship, which is apparent from a comparison of FIGS. 4A to 4C, and the distribution state of the frequency spectrum and the spectrum values vary in correlation to the waveform of the pulse wave signal d. It is therefore possible to estimate (evaluate), on the basis of frequency spectrum obtained by FFT, the state of external noise (the amount of external noise) superimposed on the pulse wave signal d.

The state of activity of the subject can also be estimated using the indexes $r5$ and $r10$ described above. This is due to the fact that when the waveform of the pulse wave signal d varies due to the state of activity of the subject, the variation appears as a variation in the frequency spectrum, and the variation in the frequency spectrum is reflected in the indexes $r5$ and $r10$.

For example, in the example of FIG. 4A, the subject is judged to be in a constant state of activity (non-constant activity factors are not present) or in a state of rest (non-constant activity factors are not present). For example, this corresponds to the subject walking with a fixed pitch and without aperiodic action such as randomly moving the wrist. The resting state (non-constant activity factors are not present) can be a case in which the subject is lying down on a bed and is not performing an aperiodic action such as randomly moving the wrist.

In the example of FIG. 4B, the subject is judged to be in a state of constant activity (non-constant activity factors are present), or in a state of rest (non-constant activity factors are present). An example of the case of constant activity can be when the subject is walking with a fixed pitch and performing aperiodic activity such as randomly moving the wrist. The resting state (non-constant activity factors are present) can be a case in which the subject is lying down on a bed and is performing a aperiodic action such as randomly moving the wrist.

In the example of FIG. 4C, the subject is judged to be in a state of non-constant activity. This corresponds to the case in which the subject is carrying out aperiodic activity, e.g., cases such as when the subject is doing exercises or playing basketball.

In this manner, the state of activity of the subject can be judged based on an evaluation of the amount of noise in the pulse wave signal d (an evaluation of the signal state).

Described next is an example in which the unworn state has been temporarily detected and the unworn state has thereafter ended, i.e., an example of judging that the unworn state has ended.

The unworn-state detector 70 carries out an unworn-state detection at predetermined time intervals (e.g., every four seconds). Consider here the case in which the unworn state has been judged by the previous detection process and the non-unworn state has been judged by the current detection process. At this time, there is a high possibility that an errant judgment will be made that the unworn state has ended (transitioned from an unworn state to a non-unworn state).

For example, in a state in which the pulse detector 100 has been left unworn on a desk, there can be cases in which the intensity of the light incident on the pulse wave sensor 10 is accidently made to fluctuate due to a person passing nearby, and made to appear as if the pulse detector 100 has been worn by the subject.

Therefore, a temporary judgment is made that the state is an unworn state, and when a non-unworn state (worn state) is subsequently judged, the unworn-state detector 70 preferably makes a further judgment using additional conditions. For example, the unworn-state detector 70 preferably examines "whether there is a spectrum equal to or greater (in magnitude) than a predetermined threshold value (in this case, a second threshold value) in the frequency spectrum obtained as a result of frequency analysis of the pulse wave signal d," and if there is such a spectrum, it is judged that the state is a non-unworn state, and if there is not such a spectrum, it is judged that the state is an unworn state.

In this manner, the conditions are weighted and judgment is made with greater care when a judgment is made as to whether the unworn state has ended. Therefore, the possibility of an errant judgment is reduced.

Described next are possible countermeasures when the unworn state has been detected by the unworn-state detector 70.

Detection of the pulse signal is carried out on the basis of past frequency analysis results, past frequency trends in the pulse signal, and other factors. In consideration of this point, when the unworn state of the pulse detector 100 has been detected by the current detection process, the unworn-state detector 70 preferably discards (e.g., initializes, erases information, or takes similar action) at least one of information 44, 45 accumulated in the pulse wave signal analyzer 42, where information 45 is frequency analysis result information of the past pulse wave signal d, and information 44 is frequency trend information that shows a trend of the frequency of the pulse signal used in the frequency analysis of the pulse wave signal d. It is more preferred that both information 44, 45 be discarded.

In the case that the unworn pulse detector 100 has again been worn by the subject, the pulse detector 100 can thereby start pulse detection processing from, e.g., an initial state. Therefore, the pulse signal can be accurately detected.

The unworn-state detector 70 can stop operation of the subject information acquisition section (pulsation count and burned calorie calculation section, which has a function for calculating at least one among the biological information of the subject and accompanying information related to the activity of the subject) when the pulse detector 100 has been detected to be in an unworn state. Accordingly, wasteful power consumption does not occur. Display (broadly defined notification) of errant information can also be prevented.

The phrase "stops operation of the subject information acquisition section" includes, e.g., not performing operation for acquiring information or preventing the operation itself by switching off the power of the subject information acquisition section 90. Switching off the power produces a greater effect of reducing power consumption.

When the pulse detector 100 is in an unworn state, a significant frequency spectrum cannot be obtained even if a frequency analysis were to be carried out. In view of this fact, the unworn-state detector 70 preferably stops the frequency analysis operation carried out by the frequency analyzer 50 when the pulse detector 100 is detected to be in an unworn state. Accordingly, wasteful power consumption does not occur. Display (broadly defined notification) of errant information can also be prevented. The phrase "stops a frequency analysis operation of the frequency analyzer" includes, e.g., not performing the frequency analysis process, or preventing the operation itself by switching off the power of the portion of the frequency analyzer 50 that carries out the frequency analysis process. Switching off the power produces a greater effect of reducing power consumption.

In the example of FIG. 1, the operation stop section 82 included in the unworn-state detector 70 stops the operation of the post-processor 60, the pulse presentation spectrum capture processor 80, and the subject information acquisition section (pulsation count and burned-calorie calculation section) 90 when the pulse detector is detected to be in an unworn state.

Figure 5:
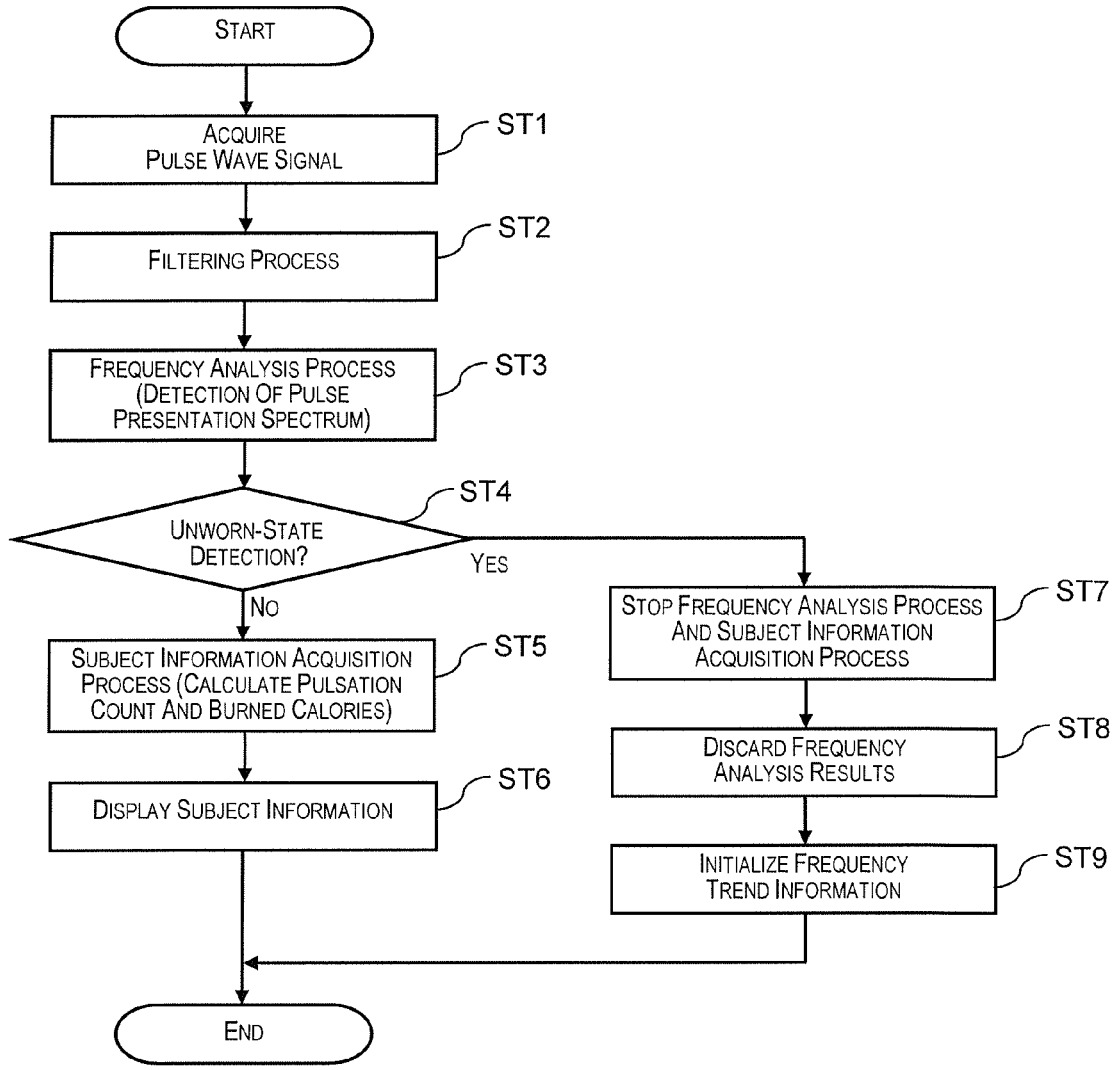
FIG. 5 is a flowchart showing an example of the processing flow that includes unworn-state detection processing in the pulse detector.

Described next is the processing flow that is included in the unworn-state detection process of the pulse detector 100. FIG. 5 is a flowchart showing an example of the processing flow that includes unworn-state detection processing in the pulse detector;

First, the pulse wave signal d is acquired by the pulse wave sensor 10 (step ST1). Next, the pulse wave signal d undergoes a filtering process performed by the filter section 30 (step ST2). A frequency spectrum is subsequently carried out by the frequency analyzer 50 (step ST3). Specifically, processes for detecting the pulse presentation spectrum are carried out (a pulse presentation spectrum identification process and a pulse presentation spectrum capture process).

Next, an unworn-state detection process is carried out by the unworn-state detector 70 (step ST4). When N is the result in step ST4, a process for acquiring subject information (a process for calculating the pulsation count and the burned calories, or another process) is carried out by the subject information acquisition section 90 (step ST5), and the subject information is then displayed (provided as notification; step ST6).

When Y is the result in step ST4, the frequency analysis process (a pulse presentation spectrum identification process and a pulse presentation spectrum capture process) is stopped, and the process for acquiring subject information (pulsation count and burned calories) is stopped (step ST7). The frequency analysis results (past frequency analysis information) are then discarded (initialized, or the like; step ST8). The frequency trend information (frequency trend information) for analyzing the pulse wave signal frequency is subsequently discarded (initialized, or the like; step ST9).

Figure 6:
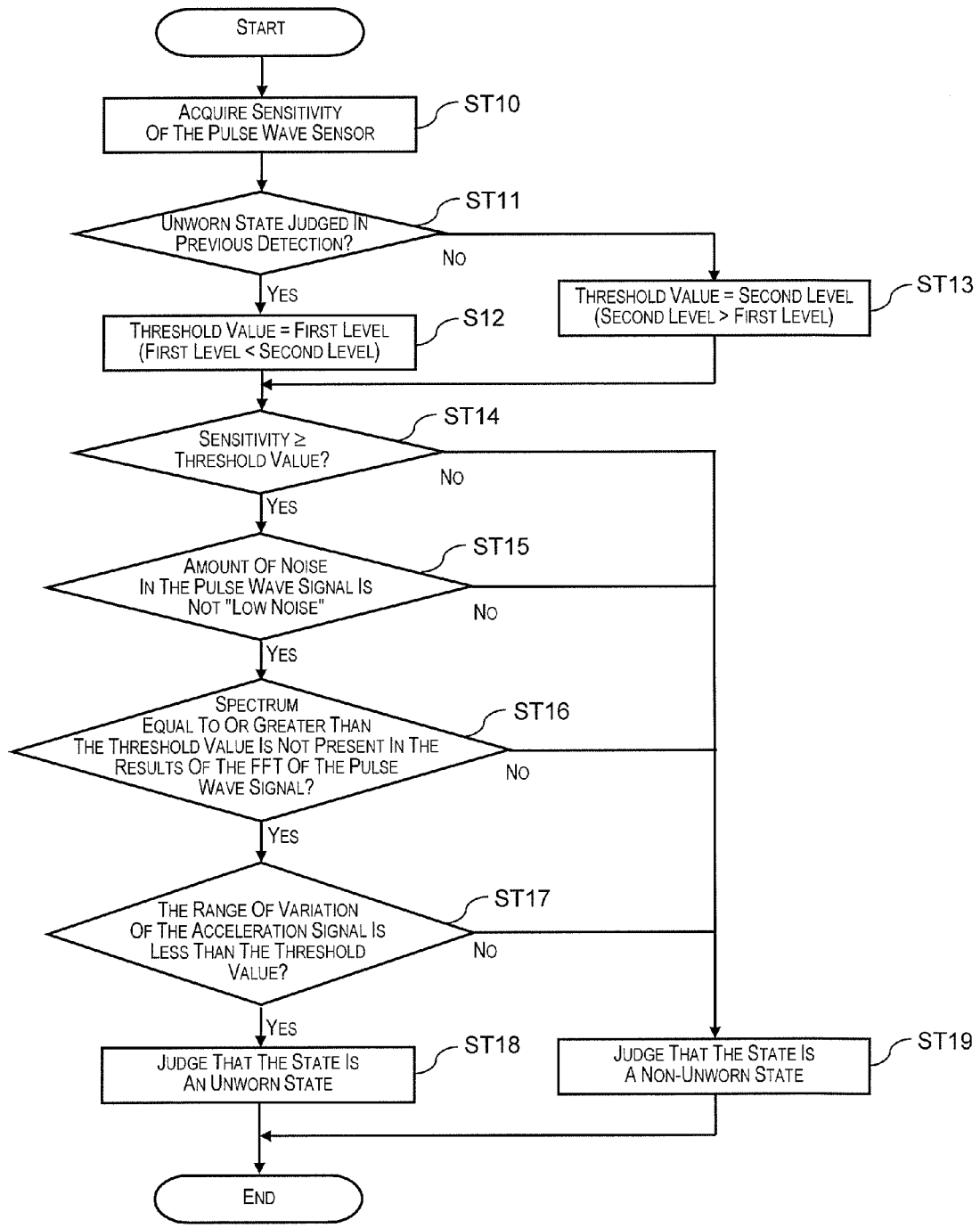
FIG. 6 is a flowchart showing an example of the processing flow of the unworn-state detection process.

Described next is the processing flow of the unworn-state detection process. FIG. 6 is a flowchart showing an example of the processing flow of the unworn-state detection process.

First, the circuit state judgment section 72 included in the unworn-state detector 70 acquires the sensitivity of the pulse wave sensor 10 (step ST10). Next, the unworn-state judgment section 78 included in the unworn-state detector 70 judges whether an unworn state has been determined by the previous (a predetermined interval of time, e.g., four seconds prior) detection process (step ST11). The level of the threshold value for judging the magnitude of the sensitivity is modified in accordance with the judgment results of step ST11. The levels of the threshold value are a first level and a second level (first level<second level).

In other words, the threshold value for judging the magnitude of the sensitivity when Y is the result in step ST11 is set to the first level (step ST12), and when N is the result, the threshold value is set (step ST13) to the second level (second level>first level). When Y is the result in step ST11, a judgment must be made in the next step as to whether the unworn state continues. It is therefore preferred that the judgment be made with greater care. Hence, when Y is the result in step ST11, the level of the threshold value is lowered, and even when the sensitivity of the pulse wave sensor fluctuates to a certain degree for some reason, the unworn state can be reliably judged in the judgment of the next step ST14 without following the fluctuation.

As described above, when the pulse detector 100 is in an unworn state, there is a high possibility that the sensitivity (GN) of the pulse wave sensor 10 is a value in a range that is impossible during ordinary measurement. In particular, noise is considerably amplified and the possibility of misdetection increases because the gain of the amplifier 4 is high when the sensitivity is near maximum. Therefore, step S14 detects whether the sensitivity of the pulse wave sensor 10 has exceeded the threshold value, i.e., whether the sensitivity (the gain value of the amplifier 4) is a large value outside the normal range. Although not shown in ST14, it is also possible to detect whether the sensitivity (the gain value of the amplifier 4) is a small value outside the normal range.

Since there is a possibility that the state is an unworn state when Y is the result in step ST14, the pulse wave signal state judgment section 76 included in the unworn-state detector 70 subsequently makes a judgment based on the amount of noise level in the pulse wave signal d and judges whether the state of the pulse wave signal d is not "low noise" (step ST15). Since there is a possibility that the state is an unworn state if Y is the result, the pulse wave signal state judgment section 76 subsequently judges whether a spectrum equal to or greater than a predetermined value (the threshold value for judging the state of the pulse wave sensor) is present in the FFT results (frequency spectrum) of the pulse wave signal d (step ST16). Since there is a possibility that the state is an unworn state if Y is the result, the body movement judgment section 74 included in the unworn-state detector 70 subsequently judges (step ST17) whether the range of variation (amplitude or signal value (spectrum value)) of the body movement sensor signal (i.e., acceleration signal) f obtained from the body movement sensor 20 (an acceleration sensor as used herein) is smaller than a predetermined threshold value (the threshold value for judging the magnitude of the acceleration signal). In the case that an X-axis direction acceleration signal, a Y-axis direction acceleration signal, and a Z-axis direction acceleration signal are included as the acceleration signal, it is possible to judge, e.g., whether all three acceleration signals are less than a threshold value.

When Y is the result in step ST17, the unworn-state judgment section 78 included in the unworn-state detector 70 judges that the pulse detector 100 is in an unworn state (step ST18).

Also, in the case that N is result in any of steps ST14 to ST17, the unworn-state judgment section 78 judges (step ST19) that the pulse detector 100 is in a non-unworn state (worn state). The processing flow described above is an example, and no limitation is imposed thereby.

Figure 7A:
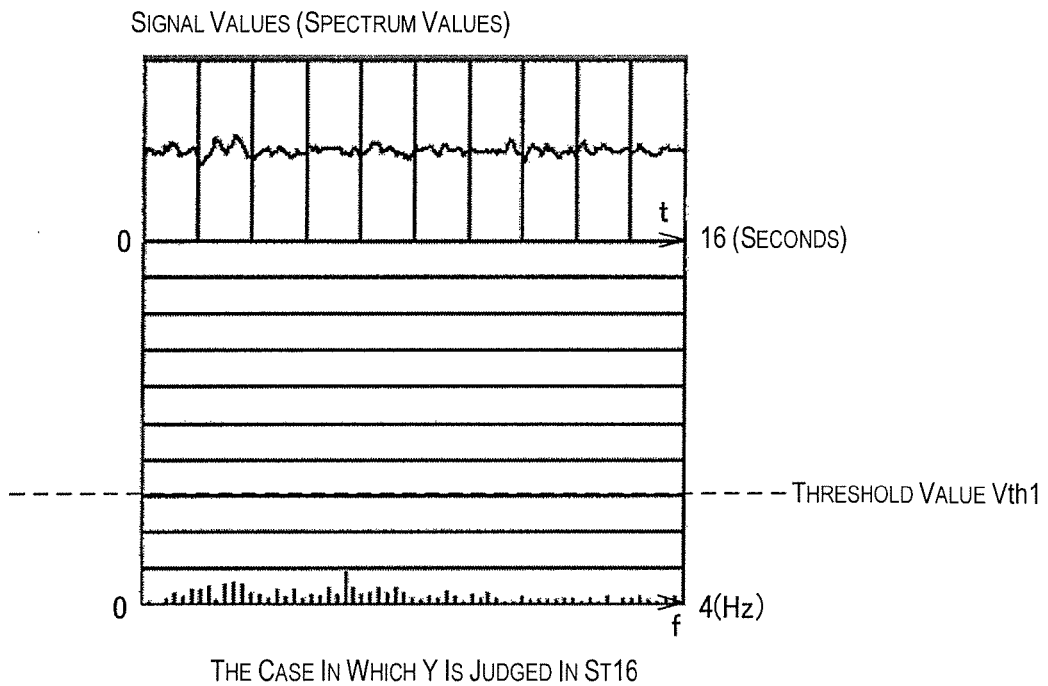
FIGS. 7A and 7B are views showing an example of when Y is judged and an example of when N is judged in step ST16 of the processing flow of FIG. 6.
Figure 7B:
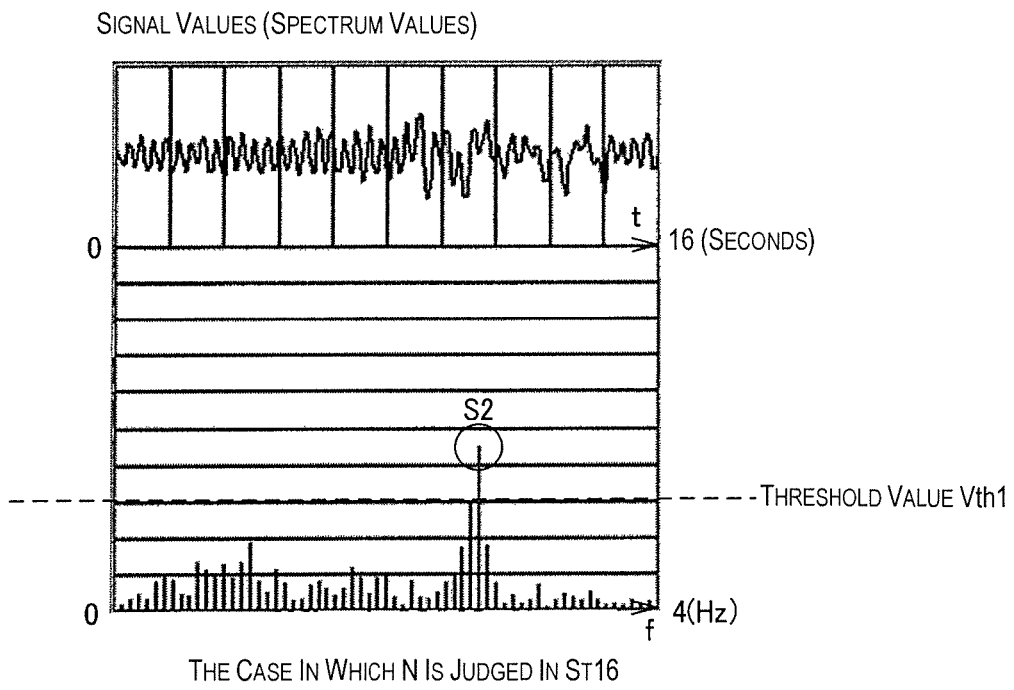

FIGS. 7A and 7B are views showing an example of when Y is judged and an example of when N is judged in step ST16 of the processing flow of FIG. 6.

In FIGS. 7A and 7B, the signal waveform of 16 seconds of the pulse wave signal d prior to FFT is shown in the upper side. The horizontal axis represents time and the vertical axis represents signal amplitude. The frequency spectrum in the frequency band 0 to 4 Hz is shown in the lower side. The horizontal axis represents the frequency and the vertical axis represents the signal value.

As described above, in step ST16 of the processing flow of FIG. 6, the pulse wave signal state judgment section 76 judges whether a spectrum equal to or greater than a predetermined threshold value (a threshold value for judging the state of the pulse wave signal) is present in the FFT results (frequency spectrum) of the pulse wave signal d. In the examples of FIGS. 7A and 7B, Vth1 is used as the predetermined threshold value. In the example of FIG. 7A, there is no spectrum having a signal value (spectrum value) that exceeds the threshold value Vth1. In contrast, in the example of FIG. 7B, there is a spectrum S2 having a signal value (spectrum value) that exceeds the threshold value Vth1. Therefore, in the example of FIG. 7A, Y is judged as the result in step ST16 of the processing flow of FIG. 6. In the example of FIG. 7B, N is judged as the result in step ST16.

Figure 8A:
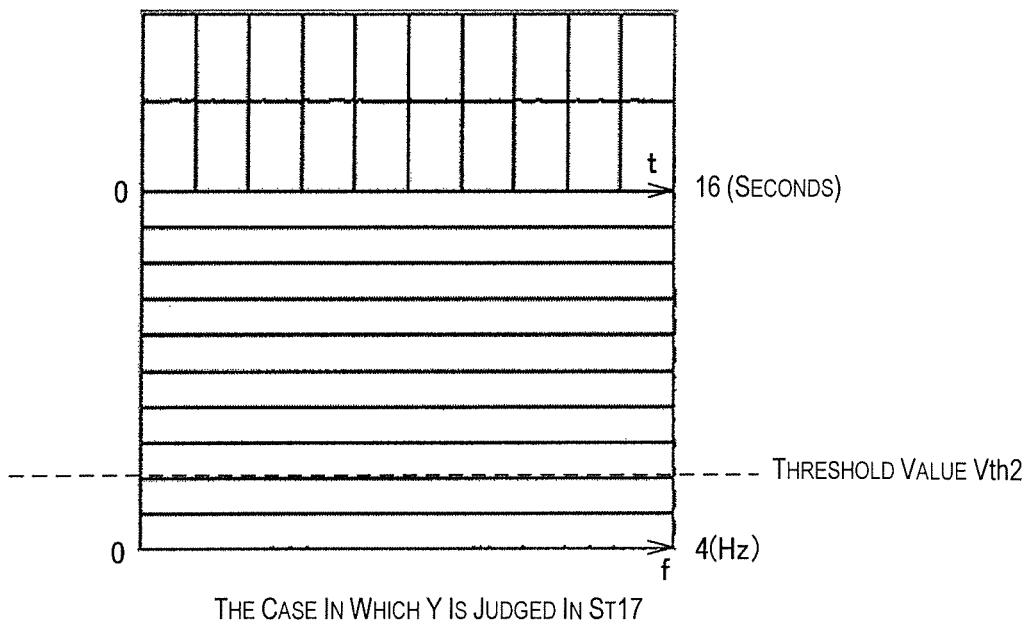
FIGS. 8A and 8B are views showing an example of when Y is judged and an example of when N is judged in step ST17 of the processing flow of FIG. 6.
Figure 8B:
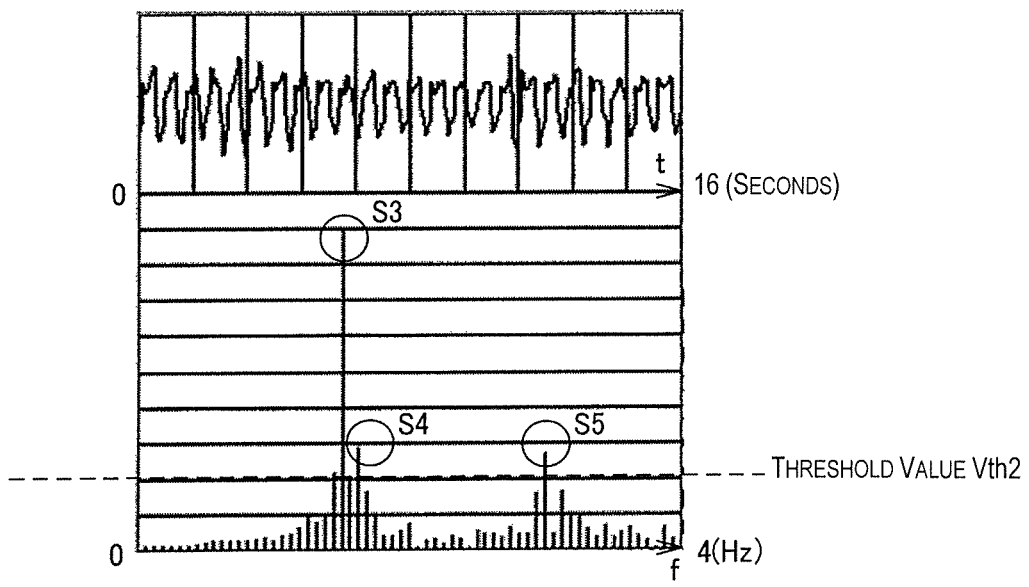

FIGS. 8A and 8B are views showing an example of when Y is judged and an example of when N is judged in step ST17 of the processing flow of FIG. 6.

In FIGS. 8A and 8B, the signal waveform of 16 seconds of the body movement sensor signal f prior to FFT is shown in the upper side. The horizontal axis represents time and the vertical axis represents signal amplitude. The frequency spectrum in the frequency band 0 to 4 Hz is shown in the lower side. The horizontal axis represents the frequency and the vertical axis represents the signal value.

As described above, in step ST17 of the processing flow of FIG. 6, the body movement judgment section 74 included in the unworn-state detector 70 judges whether the range of variation (amplitude or signal value (spectrum value)) of the body movement sensor signal (i.e., acceleration signal) f obtained from the body movement sensor 20 (an acceleration sensor as used herein) is less than a predetermined threshold value (the threshold value for judging the magnitude of the acceleration signal).

In the examples of FIGS. 8A and 8B, Vth2 is used as the predetermined threshold value. In the example of FIG. 8A, there is no spectrum having a signal value (spectrum value) that exceeds the threshold value Vth2. In contrast, in the example of FIG. 8B, there are spectrums S3, S4, and S5 having a signal value (spectrum value) that exceeds the threshold value Vth2. Therefore, in the example of FIG. 8A, Y is judged as the result in step ST17 of the processing flow of FIG. 6. In the example of FIG. 8B, N is judged as the result in step ST17.

Figure 9:
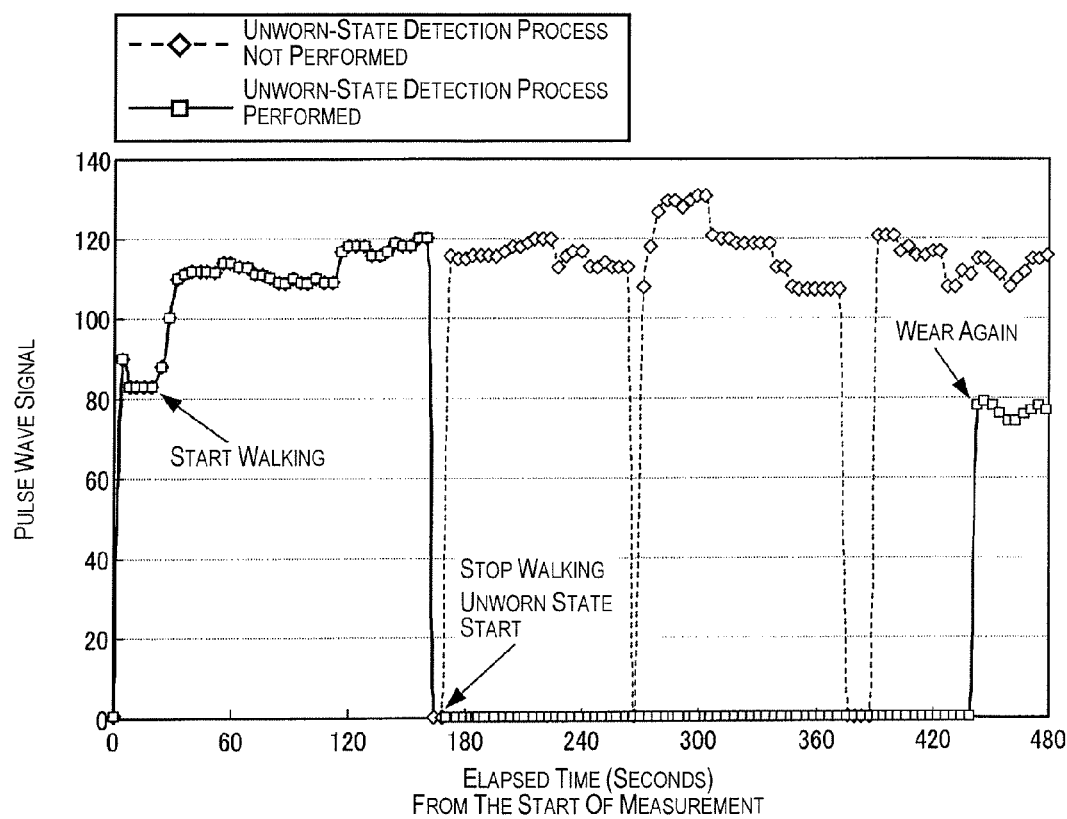
FIG. 9 is a view showing an example of pulsation measurement performed by the pulse detector.

Described next is a method for measuring pulsation by the pulse detector. FIG. 9 is a view showing an example of pulsation measurement performed by the pulse detector. The horizontal axis in FIG. 9 represents the elapsed time from the start of measurement, and the vertical axis represents the measured pulsation count (pulsations per minute).

In the example of FIG. 9, the subject (user) wears the pulse detector 100 on a wrist and starts walking at the time point that 20 seconds have elapsed after the start of measurement. This walking is continued until 164 seconds after the start of measurement. Next, the subject removes the pulse detector 100 from the wrist and places it unworn on the desk. In other words, after the start of measurement, the interval from 164 seconds to 444 seconds is an interval in which the pulse detector 100 is in an unworn state. In this interval, the subject keeps an upright state without moving.

The subject again wears the pulse detector 100 on the wrist when 444 seconds have elapsed after the start of measurement. When the pulse detector 100 is worn, the subject is in an upright state without moving.

In the example of FIG. 9, the solid line represents the change in the pulsation count that is measured when the unworn-state detector 70 carries out an unworn-state detection process. The dotted line represents change in the pulsation count measured in the case that the unworn-state detector 70 does not carry out the unworn-state detection process (comparative example). Detection of the pulsation count which is based on the pulse signal is carried out in four-second intervals (i.e., once every four seconds), and the unworn-state detection process performed by the unworn-state detector 70 is also similarly carried out in four-second intervals.

In FIG. 9, there is a location in which the pulsation count is zero (pulsation count=0). A pulsation count of zero means that the pulsation count could not be calculated. The reason for this is that, e.g., a significant signal spectrum that corresponds to the pulse signal could not be found as a result of a frequency analysis of the pulse wave signal d, and it is possible that pulse detection has failed or that the pulsation count calculation process was stopped as a result of the unworn-state detection process.

In the example of FIG. 9, when the unworn-state detector 70 does not carry out unworn-state detection (in the case of the comparative example), the pulsation count is measured for most of the interval (the interval of 164 seconds to 444 seconds after the start of measurement) in which the pulse detector 100 is in an unworn state. In other words, the pulsation count of about 105 to 115 continues to be measured. Naturally, this pulsation count is an errant pulsation count, and the meaning of the measurement is lost. Such a result is obtained because the frequency analyzer 50 references past frequency trend information of the pulse signal or performs other processes and continues the process of detecting the pulse signal even when the pulse detector in an unworn state.

On the other hand, when the unworn-state detector 70 carries out an unworn-state detection process, the pulsation count is zero in the interval (the interval of 164 seconds to 444 seconds after the start of measurement) in which the pulse detector 100 is in an unworn state. At the time point where 444 seconds have elapsed after the start of measurement, the pulse detector 100 correctly measures the pulsation count (about 80) of the subject in an upright state when the subject again wears the pulse detector 100 on the wrist. In the comparative example, a pulsation count of about 105 to 115 is measured at the time point where 444 seconds have elapsed after the start of measurement, and the pulsation count is not correctly measured.

As described above, past frequency analysis results and the frequency trend information of the pulse signal are discarded in the case that an unworn state has been judged by the unworn-state detector 70. Therefore, the pulse detector 100 can start detection of the pulsation count from, e.g., an initialized state when the subject again wears the pulse detector 100 on the wrist (when 444 seconds have elapsed after the start of measurement), and the pulsation count can be correctly measured without following past errant information.

In this manner, in accordance with the present embodiment, it is possible to detect that, e.g., the pulse detector is in an unworn state. For example, it is possible to detect with high accuracy the unworn state of the pulse detector without the use of e.g., a special configuration.

For example, the pulse detector 100 of the present embodiment can differentiate between when the subject is resting or sleeping and when the pulse detector 100 is in an unworn state, and it is therefore possible to detect the unworn state (judge the unworn state/non-unworn state) with high accuracy.

When the unworn state continues, e.g., in the case that the intensity of outside light incident on the pulse detector 100 fluctuates and noise is inputted, the possibility that an errant judgment (judgment that the worn state has been restored) will be made is reduced because the unworn-state detector 70 carefully judges whether the unworn state has ended (e.g., makes a judgment with consideration given to the analysis results of the pulse wave signal or other factors).

When the pulse detector 100 is in an unworn state, the display of errant measurement results is prevented and power savings in the pulse detector 100 can be realized because calculation and display of the pulsation count and burned calories (acquisition of subject information) are stopped. Longer continuous pulse detection or the like using the pulse detector 100 is made possible when the pulse detector 100 is made to save power.

Figure 10A:
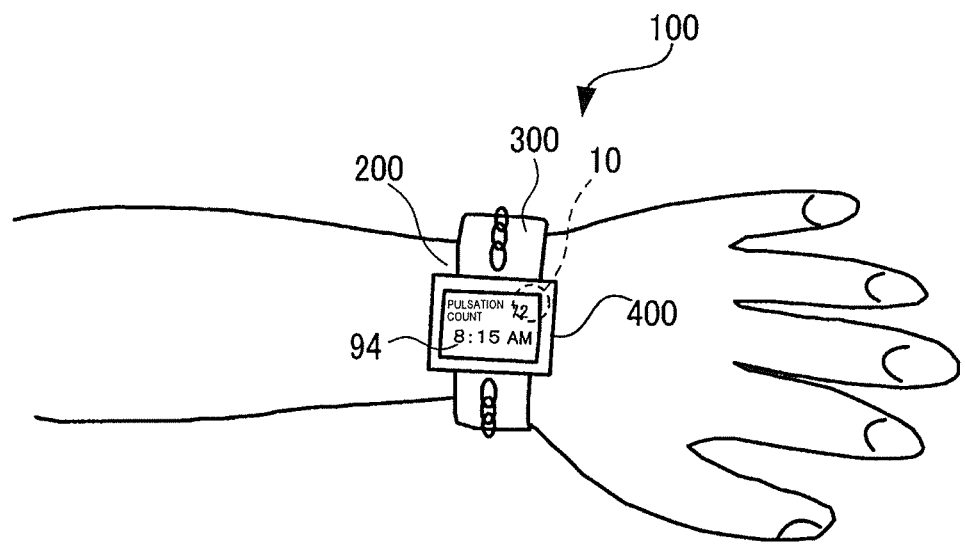
FIGS. 10A and 10B are views showing an example of the pulse detector being worn by the subject.
Figure 10B:
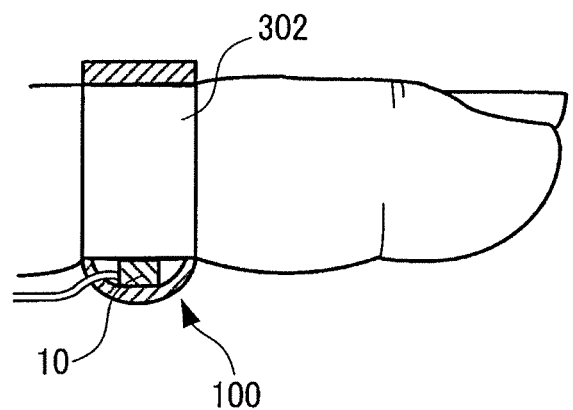

FIGS. 10A and 10B are views showing an example of the pulse detector being worn by the subject.

The example of FIG. 10A is an example of a wristwatch-type pulse detector. A base section 400 that includes the pulse wave sensor 10 and the display section 94 is worn on the left wrist 200 of the subject (user) with the aid of a wristband 300.

The example of FIG. 10B is an example of a finger-worn-type pulse detector. The pulse wave sensor 10 is provided to the bottom section of a ring-shaped guide 302 into which the fingertip of the subject is inserted.

The present embodiment is described in detail above, and it is readily apparent to a person skilled in the art that various modifications can be made without substantively departing from novel features and effects of the invention. Therefore, any such modifications are understood to reside with the scope of the invention. In the specification and drawings, terms described together with different terms having a wider definition or similar definition can be substituted at least once for the different terms in any location in the specification and drawings.

What is claimed is:

1. A pulse detector that detects a pulse signal originating from a pulse of a subject and an unworn state of the pulse detector, the unworn state being a state in which the pulse detector has been removed from the subject, the pulse detector comprising:
   a pulse wave sensor outputting a pulse wave signal that includes the pulse signal;
   an amplifier amplifying the pulse signal;
   a pulse wave sensor sensitivity adjustment section that adjusts a sensitivity of the pulse wave sensor based on an input signal to the pulse wave sensor or an intensity of the pulse wave signal, the sensitivity being a gain of the amplifier;
   a body movement sensor that detects body movement of the subject and outputs a body movement sensor signal originating from the body movement;
   an unworn-state detector that detects, at predetermined time intervals, an unworn state;
   wherein to detect the unworn state at a current timing, which is subsequent to a previous timing with one of the predetermined time intervals between the previous timing and current timing, the unworn state detector;
   obtains the sensitivity,
   determines whether or not the unworn state has been detected at the previous timing,
      wherein in response to determining that the unworn-state detector has detected the unworn state at the previous timing, setting a first level as a sensitivity threshold,
      wherein in response to determining that the unworn-state detector has not detected the unworn state at the previous timing, setting a second level, which is greater than the first level, as the sensitivity threshold; and
   wherein the unworn-state detector detects the unworn state at the current timing in response to determining that the sensitivity is greater than the sensitivity threshold, and determining that a level of the body movement sensor signal outputted from the body movement sensor is less than a predetermined movement threshold value.

2. The pulse detector according to claim 1, wherein
the pulse detector has a subject information acquisition section that acquires at least one of biological information of the subject and accompanying information related to activity by the subject; and
the unworn-state detector stops operation of the subject information acquisition section when detecting the unworn state.

3. The pulse detector according to claim 1, further comprising a frequency analyzer that performs frequency analysis at the predetermined time intervals based on the pulse wave signal or a filtered signal obtained by subjecting the pulse wave signal to filtering for suppressing noise included in the pulse wave signal, wherein the unworn-state detector stops a frequency analysis operation carried out by the frequency analyzer when the unworn state has been detected.

4. The pulse detector according to claim 1, wherein the pulse wave sensor sensitivity adjustment section adjusts the gain of the amplifier such that the pulse wave sensor outputs the pulse wave signal having a fixed level.

5. The pulse detector according to claim 1, further comprising:

a frequency analyzer that performs frequency analysis at the predetermined time intervals based on the pulse wave signal or a filtered signal obtained by subjecting the pulse wave signal to filtering for suppressing noise included in the pulse wave signal, wherein the unworn-state detector detects the unworn state based on the sensitivity being greater than the sensitivity threshold, the body movement sensor signal being less than the predetermined movement threshold value, and the result of the frequency analysis of the pulse wave signal performed by the frequency analyzer.

6. The pulse detector according to claim 5, wherein when detecting the unworn state to be in effect at the current timing, the unworn state detector discards at least one among results of the frequency analysis of the pulse wave signal, and information showing a trend of a frequency of the pulse signal used in the frequency analysis of the pulse wave signal, which have been accumulated previously.

7. The pulse detector according to claim 5, wherein the frequency analysis includes a frequency spectrum, and wherein the detecting the unworn state based on also the result of the frequency analysis includes the frequency spectrum not including a spectrum equal to or greater than a first spectrum threshold value.

8. The pulse detector according to claim 5, wherein the frequency analysis includes a frequency spectrum, and wherein the detecting the unworn state based on also the result of the frequency analysis includes the frequency spectrum not including a spectrum equal to or greater than a first spectrum threshold value; and an amount of noise included in the pulse wave signal is judged to be equal to or greater than a predetermined amount on the basis of the frequency spectrum.

9. The pulse detector according to claim 7, wherein the frequency spectrum includes a spectrum equal to or greater than a second spectrum threshold value; the unworn state detector detects the unworn state not to be in effect at the current timing when the unworn state was in effect in the previous timing, the sensitivity is greater than the sensitivity threshold, and the frequency spectrum does not include a spectrum equal to or greater than the second spectrum threshold value.

* * * * *